United States Patent
Guo et al.

(10) Patent No.: US 11,640,849 B2
(45) Date of Patent: May 2, 2023

(54) METHODS FOR HISTOLOGICAL DIAGNOSIS AND TREATMENT OF DISEASES

(71) Applicant: CROWN BIOSCIENCE, INC. (TAICANG), Jiangsu (CN)

(72) Inventors: Sheng Guo, Jiangsu (CN); Henry Qixiang Li, Oceanside, CA (US)

(73) Assignee: CROWN BIOSCIENCE, INC. (TAICANG), Jiangsu (CN)

( * ) Notice: Subject to any disclaimer, the term of this patent is extended or adjusted under 35 U.S.C. 154(b) by 158 days.

(21) Appl. No.: 15/756,979

(22) PCT Filed: Sep. 9, 2016

(86) PCT No.: PCT/CN2016/098593
§ 371 (c)(1),
(2) Date: Mar. 1, 2018

(87) PCT Pub. No.: WO2017/041746
PCT Pub. Date: Mar. 16, 2017

(65) Prior Publication Data
US 2018/0247014 A1    Aug. 30, 2018

(30) Foreign Application Priority Data

Sep. 10, 2015  (WO) ............... PCT/CN2015/089349
Apr. 21, 2016  (WO) ............... PCT/CN2016/079859

(51) Int. Cl.
| | |
|---|---|
| *C12Q 1/68* | (2018.01) |
| *G16B 30/10* | (2019.01) |
| *G16B 30/00* | (2019.01) |
| *G16B 40/00* | (2019.01) |
| *G16B 45/00* | (2019.01) |
| *C12Q 1/6886* | (2018.01) |
| *G16B 40/20* | (2019.01) |

(52) U.S. Cl.
CPC ........... *G16B 30/10* (2019.02); *C12Q 1/6886* (2013.01); *G16B 30/00* (2019.02); *G16B 40/00* (2019.02); *G16B 40/20* (2019.02); *G16B 45/00* (2019.02); *C12Q 2600/106* (2013.01); *C12Q 2600/158* (2013.01)

(58) Field of Classification Search
CPC ........ G16B 30/00; G16B 40/00; G16B 45/00; C12Q 1/6886; C12Q 2600/106; C12Q 2600/158
See application file for complete search history.

(56) References Cited

U.S. PATENT DOCUMENTS

| | | | | |
|---|---|---|---|---|
| 8,252,538 | B2* | 8/2012 | Croce ................. | C12Q 1/6886 435/6.1 |
| 9,670,549 | B2* | 6/2017 | Mock .............. | G01N 33/57484 |
| 2005/0048542 | A1* | 3/2005 | Baker .................. | G16B 40/00 435/6.14 |
| 2007/0031876 | A1* | 2/2007 | Lin ..................... | C12Q 1/6886 435/6.14 |
| 2010/0284915 | A1* | 11/2010 | Dai ...................... | C12Q 1/6886 424/9.1 |
| 2013/0296198 | A1* | 11/2013 | Gordon ............... | C12Q 1/6886 506/38 |
| 2014/0297194 | A1* | 10/2014 | Yang .................... | G16B 25/00 702/19 |
| 2014/0357660 | A1* | 12/2014 | Mock .................. | C12Q 1/6886 514/291 |

FOREIGN PATENT DOCUMENTS

| | | | |
|---|---|---|---|
| WO | 2008021115 A2 | 2/2008 | |
| WO | WO-2008021115 A2 * | 2/2008 | ....... G01N 33/57423 |
| WO | 2012135397 A2 | 10/2012 | |

OTHER PUBLICATIONS

Xu et al in "A Comparative Study of Gene-Expression Data of Basal Cell Carcinoma and Melanoma Reveals New Insights about the Two Cancers", (PLoS ONE, vol. 7, No. 1, Jan. 25, 2012, p. e30750; IDS reference). (Year: 2012).*
The Cancer Genome Atlas Research Network et al The Cancer Genome Atlas Pan-Cancer analysis project, (Nature Genetics, Oct. 2013, vol. 45, No. 10, pp. 1113-1120; IDS reference). (Year: 2013).*
The Cancer Genome Atlas Research Network et al., "The Cancer Genome Atlas Pan-Cancer Analysis Project" Nature Genetics, Oct. 31, 2013 (Oct. 31, 2013), No. 10 vol. 45, pp. 1113-1120.
International Search Report and Written Opinion for PCT/CN2016/098593.

(Continued)

*Primary Examiner* — Catherine S Hibbert
(74) *Attorney, Agent, or Firm* — Jun He Law Offices P.C.; Yi Zhang

(57) ABSTRACT

The present disclosure provides a diagnostic method based on pairwise comparison of cancers using transcriptome expression data. In one embodiment, the method comprises the steps of: obtaining a first gene expression profile of a first cancer sample having a first cancer type; obtaining a second gene expression profile of a second cancer sample having a second cancer type, wherein the second cancer type is different from the first cancer type; comparing said first gene expression profile with said second gene expression profile; and selecting N genes that are most differentially expressed in the first and the second gene expression profiles to generate pairwise differentially expressed genes (DEGs), wherein N is an integer between 10 and 100.

10 Claims, 15 Drawing Sheets

(56) References Cited

OTHER PUBLICATIONS

Kun Xu et al: "A Comparative Study of Gene-Expression Data of Basal Cell Carcinoma and Melanoma Reveals New Insights about the Two Cancers", PLOS ONE, vol. 7, No. 1, Jan. 25, 2012 (Jan. 25, 2012), p. e30750, XP055557254, DOI: 10.1371/journal.pone. 0030750. p. 8, left-hand column, paragraphs 2, 3; figures 1, S5; table S1, S3.

Kun Xu et al: "A Comparative Analysis of Gene-Expression Data of Multiple Cancer Types", PLOS ONE, vol. 5, No. 10, Oct. 27, 2010 (Oct. 27, 2010), p. e13696, XP055198181, DOI: 10.1371/journal. pone.0013696.the whole document.

Martinez et al: "Comparison of gene 1-15 expression patterns across twelve tumor types identifies a cancer supercluster characterized by TP53 mutations and cell cycle defects", ONCOGENE, vol. 34, No. 21, Aug. 4, 2014 (Aug. 4, 2014), pp. 2732-2740, XP055556415, London, ISSN: 0950-9232, D0I: 10.1038/onc.2014.216. the whole document.

The extended European Search Report of PCT Application No. PCT/CN2016/098593, dated Mar. 7, 2019.

\* cited by examiner

METHODS FOR HISTOLOGICAL DIAGNOSIS AND TREATMENT OF DISEASES

CROSS-REFERENCE TO RELATED APPLICATIONS

The present application is a national phase of International Application PCT/CN2016/098593, filed Sep. 9, 2016, which claims the benefit of International Applications PCT/CN2015/089349, filed Sep. 10, 2015, and PCT/CN2016/079859, filed Apr. 21, 2016, both of which are incorporated herein by reference in their entirety.

FIELD OF THE INVENTION

The present invention generally relates to diagnosing and treating diseases, such as cancer.

BACKGROUND OF THE INVENTION

Cancers are heterogeneous with diverse pathogenesis. The accurate diagnosis of cancers helps to understand disease development and prognosis, thus guide precision treatments. Current clinical diagnosis is primarily based on anatomic locations (organs) and histopathology (morphology of cancerous tissues and cells), which may not be accurate. For example, a metastasis could be misdiagnosed if the morphology is insufficient to identify its origin. An improved diagnostic method is therefore needed. Transcriptome sequencing (RNA-seq or microarray) profiles gene expression, which may be used to describe molecular pathology of cancers and diagnose disease. The Cancer Genome Atlas (TCGA) project has generated abundant genomic data for human cancers of various histopathology types and enabled exploring cancer molecular pathology through big data analysis. It remains a challenge, however, to correlate differentially expressed genes to cancer pathology, such as the tissue origin of the cancer. Therefore, there is a need to develop new methods for diagnosing cancers based on the systematically confirmed correlation between histopathology and molecular pathology.

BRIEF SUMMARY OF THE INVENTION

In one aspect, the present disclosure provides a method comprising the steps of:
  obtaining a first gene expression profile of a first cancer sample having a first cancer type;
  obtaining a second gene expression profile of a second cancer sample having a second cancer type, wherein the second cancer type is different from the first cancer type;
  comparing said first gene expression profile with said second gene expression profile; and
  selecting N genes that are most differentially expressed in the first and the second gene expression profiles to generate pairwise differentially expressed genes (DEGs), wherein N is an integer between 10 and 100.

In certain embodiments, the cancer sample used herein is not a cancer cell line.

In certain embodiments, the cancer sample used herein is a surgical removal sample or biopsy sample from a cancer patient or a patient derived xenograft (PDX).

In certain embodiments, N is between 20 and 80. In certain embodiments, N is around 50.

In certain embodiments, the gene expression profile described herein is obtained by transcriptome RNA sequencing or microarray. In certain embodiments, the gene expression profile described herein is obtained from the cancer genome atlas (TCGA) dataset.

In certain embodiments, the N genes most differentially expressed are selected by ranking the expression difference of each gene using t-test, Mann-Whitney U test, or other tests that compare mean and median between 2 or more groups.

In certain embodiments, the cancer type described herein is colon adenocarcinoma (COAD), rectum adenocarcinoma (READ), lung adenocarcinoma (LUAD), lung squamous cell carcinoma (LUSC), head and neck squamous cell carcinoma (HNSC), liver hepatocellular carcinoma (LIHC), or pancreatic adenocarcinoma (PAAD).

In certain embodiments, the method described above further comprises diagnosing a cancer based on the expression of the pairwise DEGs.

In another aspect, the present disclosure provides a method comprising:
  obtaining a first gene expression profile of a first cancer sample having a first cancer type;
  obtaining a second gene expression profile of a second cancer sample having a second cancer type, wherein the second cancer type is different from the first cancer type;
  obtaining a third gene expression profile of a third cancer sample having a third cancer type, wherein the third cancer type is different from the first and the second cancer type;
  comparing said first gene expression profile with said second gene expression profile;
  selecting $N_1$ genes that are most differentially expressed in the first and the second gene expression profiles to generate first pairwise DEGs, wherein $N_1$ is an integer between 10 and 100;
  comparing said first gene expression profile with said third gene expression profile;
  selecting $N_2$ genes from the gene set that are most differentially expressed in the first and the third gene expression profiles to generate second pairwise DEGs, wherein $N_2$ is an integer between 10 and 100;
  comparing said second gene expression profile with said third gene expression profile;
  selecting $N_3$ genes from the gene set that are most differentially expressed in the second and the third gene expression profiles to generate third pairwise DEGs, wherein $N_3$ is an integer between 10 and 100; and
  generating a signature genes that comprises the first, second and third pairwise DEGs.

In certain embodiments, the signature genes have m genes, wherein m is an integer between 5 to 5000.

In certain embodiments, the method described above further comprises diagnosing a cancer based on the expression of the signature genes.

In yet another aspect, the present disclosure provides a method for treating a cancer in a subject, comprising diagnosing the cancer type in the subject by the method as described herein, and administering a drug that can effectively treat the cancer type.

In yet another aspect, the present disclosure provides a method for treating a first cancer type in a subject, wherein the first cancer type has the same expression profile of pairwise DEGs as a second cancer type, the method comprising administering to the subject a drug that can effectively treat the second cancer type.

In one embodiment, the first cancer type is colon adenocarcinoma (COAD), and the second cancer type is rectum adenocarcinoma (READ). In one embodiment, the first cancer type is rectum adenocarcinoma (READ), and the second cancer type is colon adenocarcinoma (COAD).

In one embodiment, the first cancer type is neck squamous cell carcinoma (HNSC), and the second cancer type is lung squamous cell carcinoma (LUSC). In one embodiment, the first cancer type is lung squamous cell carcinoma (LUSC), and the second cancer type is neck squamous cell carcinoma (HNSC).

DETAILED DESCRIPTION OF THE INVENTION

Figure 1A:
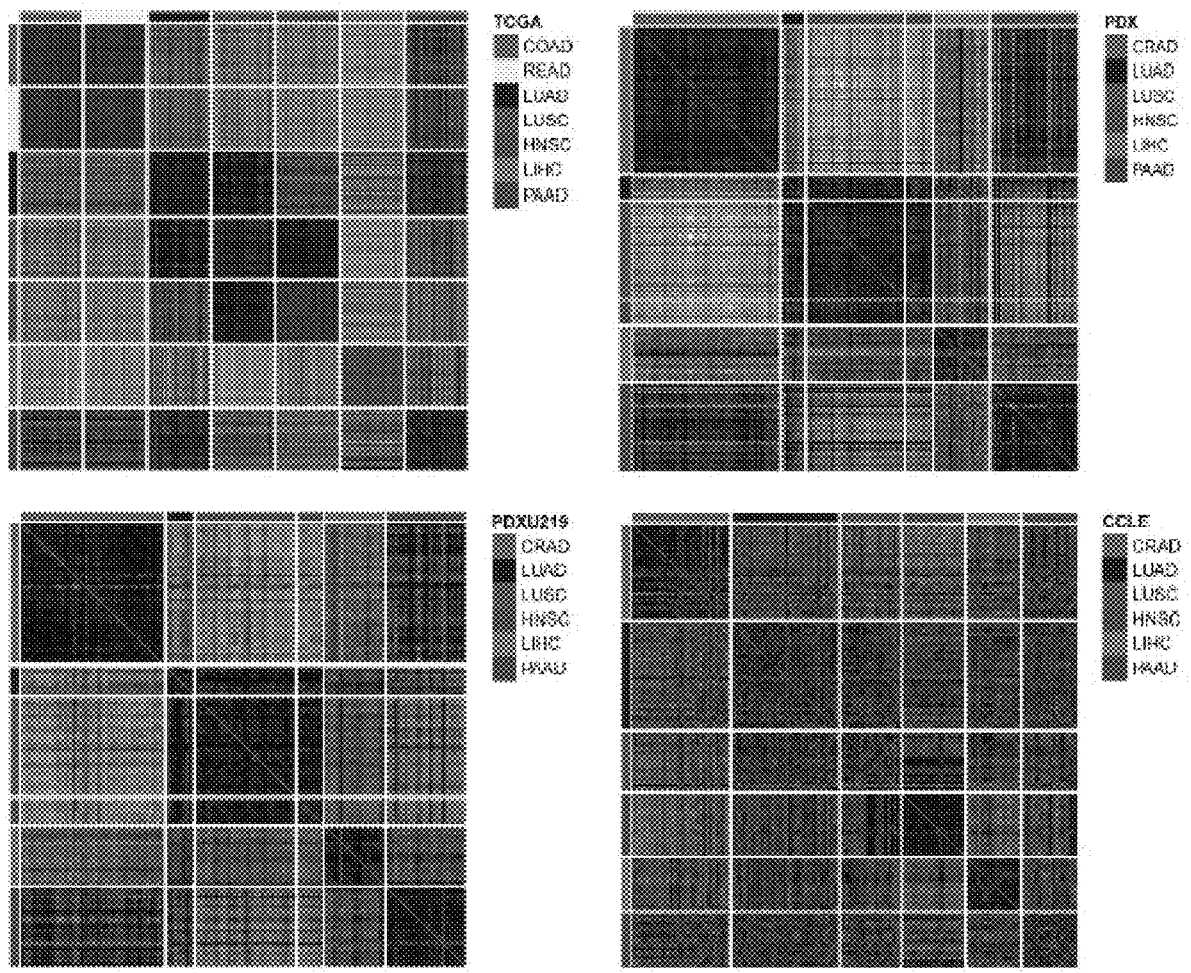
FIG. 1A illustrates comparison of gene expression for TCGA patient samples profiled by RNA-Seq, PDXs profiled by RNA-seq (PDX), PDXs profiled by microarray (PDXU219), and cancer cell lines profiled by microarray (CCLE). The number of pairwise DEGs is 50, at which there are 686 unique genes. In the heatmaps, Pearson correlation coefficient between two samples is color-coded; the length of a color bar on the top or left is proportional to sample size within a dataset.
Figure 1B:
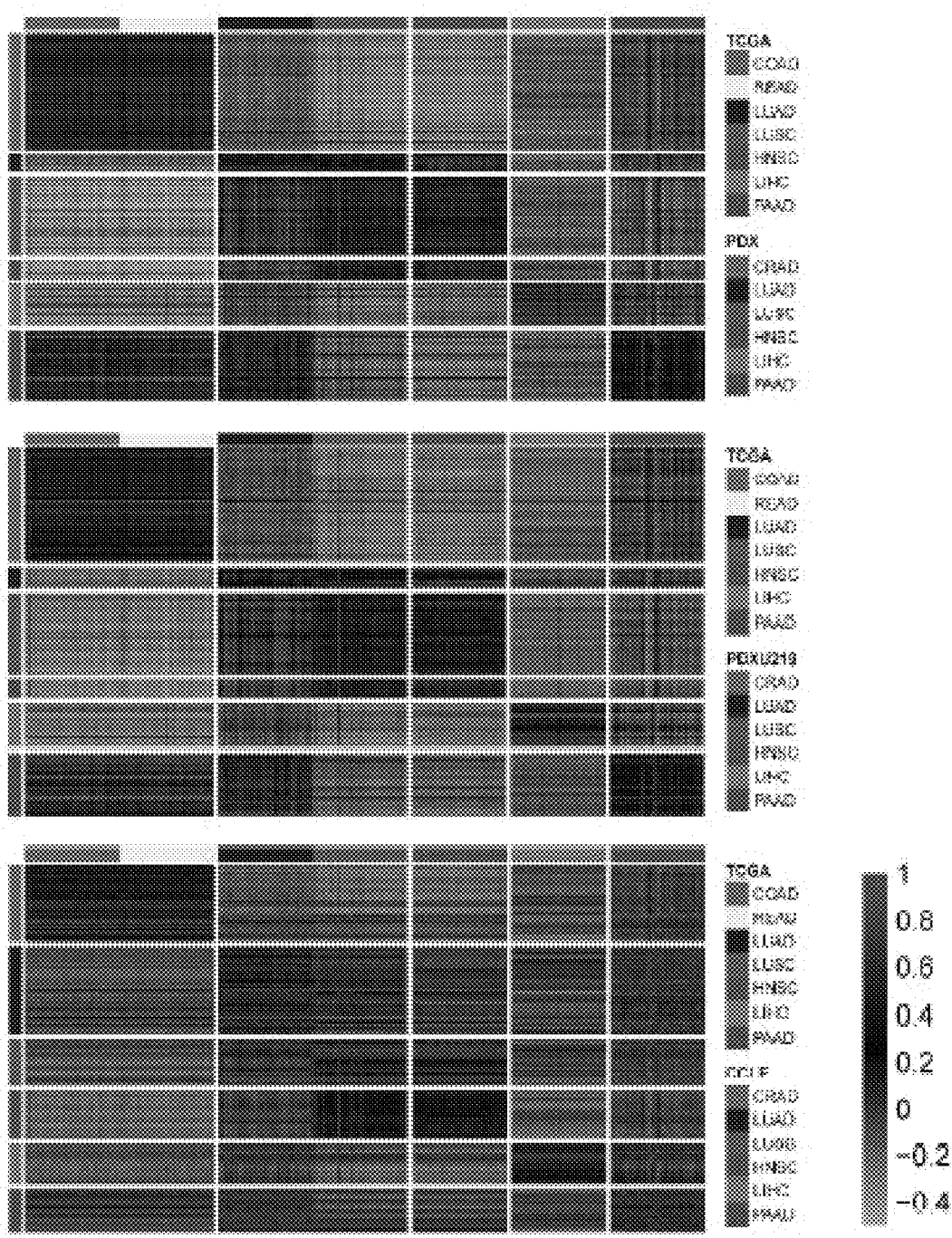
FIG. 1B illustrates comparison of gene expression between TCGA and the other 3 datasets. The number of pairwise DEGs is 50, at which there are 686 unique genes. In the heatmaps, Pearson correlation coefficient between two samples is color-coded; the length of a color bar on the top or left is proportional to sample size within a dataset.

In the Summary of the Invention above and in the Detailed Description of the Invention, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or particular claim, that feature can also be used, to the extent possible, in combination with and/or in the context of other particular aspects and embodiments of the invention, and in the invention generally.

The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

Where a range of value is provided, it is understood that each intervening value, to the tenth of the unit of the lower limit unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, the embodiments described herein can be practiced without there specific details. In other instances, methods, procedures and components have not been described in detail so as not to obscure the related relevant function being described. Also, the description is not to be considered as limiting the scope of the implementations described herein. It will be understood that descriptions and characterizations of the embodiments set forth in this disclosure are not to be considered as mutually exclusive, unless otherwise noted.

With the available of The Cancer Genome Atlas (TCGA) datasets from multiple genomic profiling platforms, molecular taxonomy methods have been developed and tested (Hoadley K A, Yau C, Wolf D M, Cherniack A D, Tamborero D, Ng S, et al., "Multiplatform analysis of 12 cancer types reveals molecular classification within and across tissues of origin" Cell (2014) 158(4):929-44; Cancer Genome Atlas Research Network, "Comprehensive molecular characterization of gastric adenocarcinoma" Nature (2014) 513 (7517):202-9). Many such methods analyze samples from multiple cancer types simultaneously, and may be biased toward certain types.

The present disclosure provides new methods for cancer diagnosis based on most differentially expressed genes (DEGs) per pairwise comparisons. The methods disclosed herein are based on the finding that the expression of pairwise DEGs is highly correlated within types and of low correlation between types, thus establishing molecular specificity of cancer types and an alternative diagnostic method largely equivalent to histopathology. The methods disclosed herein are also based on the finding that pairwise DEGs derived from surgery removal or autopsy samples of patient or patient derived xenografts (PDXs), but not derived from cancer cell lines provide reliable biomarker metrics for cancer diagnosis. We found highly similar patterns for within- and between-type correlation between PDXs and patient samples, confirming the high relevance of PDXs as surrogate experimental models for human diseases. In contrast, cancer cell lines have drastically reduced expression similarity to both PDXs and patient samples.

In one aspect, the present disclosure provides a new diagnostic method based on pairwise comparison of cancers using transcriptome expression data, an approach different from the methods using multiple types of genomic data and complex algorithms more commonly used (see Hoadley K A, Yau C, Wolf D M, Cherniack A D, Tamborero D, Ng S, et al., "Multiplatform analysis of 12 cancer types reveals molecular classification within and across tissues of origin" Cell (2014) 158(4):929-44; Cancer Genome Atlas Research Network, "Comprehensive molecular characterization of gastric adenocarcinoma" Nature (2014) 513(7517):202-9). Compared to these methods and algorithms, the method disclosed herein has the advantage of being simple and unbiased in assessing and describing cancer type specificity. The method disclosed herein is able to define cancer type specificity and establish near equivalency between the resulted molecular classification and the traditional disease classification based on tumor origin and histopathology, thus providing a molecular alternative to traditional histopathology for diagnosing cancer with better accuracy and precision. Since there is little limitation to the level of classifications done by the molecular pathology method disclosed herein, it can reach a degree significantly beyond existing histopathology based method, and can be more accurate, reliable, and with better objectivity. The advantage of this molecular diagnosis method can be exemplified by its ability to correct the wrong diagnosis made by hospitals. It also could be used for molecular diagnosis, a complement to the existing one based on histopathology, with certain superiority.

In certain embodiments, the method disclosed herein comprises the steps of:
  obtaining a first gene expression profile of a first cancer sample having a first cancer type;
  obtaining a second gene expression profile of a second cancer sample having a second cancer type, wherein the second cancer type is different from the first cancer type;
  comparing said first gene expression profile with said second gene expression profile; and
  selecting N genes that are most differentially expressed in the first and the second gene expression profiles to generate pairwise differentially expressed genes (DEGs), wherein N is an integer between 10 and 100.

As used herein, the term "gene" refers broadly to any nucleic acid associated with a biological function. Genes typically include coding sequences and/or the regulatory sequences required for expression of such coding sequences. The term gene can apply to a specific genomic sequence, as well as to a cDNA or an mRNA encoded by that genomic sequence. "Gene expression" refers to the process by which information from a gene is used in the synthesis of a functional product, including protein and functional RNA (e.g., tRNA, snRNA, and microRNA). In certain embodiments, the expression level of a gene can be measured by the transcript (e.g. mRNA) of the gene or the derivative thereof (e.g. cDNA).

"Gene expression profile," as used herein, refers to the measurement of the expression level of a plurality (e.g., more than 100, more than 500, more than 1,000, more than 2,000, more than 5,000, more than 10,000, more than 20,000) of genes, so as to create a global picture of gene expression in a cell (or cells). As disclosed herein, a gene expression profile can be obtained using methods known in the art, such as DNA microarray technology (see, e.g., Pollack J R et al., "Genome-wide analysis of DNA copy-number changes using cDNA microarrays" Nat Genet (1999) 23(1): 41-46). Sequence-based technologies used for gene expression profiling include, without limitation, serial analysis of gene expression (SAGE) and RNA-seq. The methods for gene expression profile analysis has been previously described (see, e.g., Yang M et al., "Overcoming erlotinib resistance with tailored treatment regimen in patient-derived xenografts from naive Asian NSCLC patients". International journal of cancer (2013) 132(2):E74-84; Chen D et al., "A set of defined oncogenic mutation alleles seems to better predict the response to cetuximab in CRC patient-derived xenograft than KRAS 12/13 mutations" Oncotarget (2015) 6(38):40815-21).

The methods of comparing two gene expression profiles are known in the art (see, e.g., Robinson M D and Smyth G K, "Small-sample estimation of negative binomial dispersion, with applications to SAGE data" Biostatistics (2008) 9(2):321-32). In certain embodiments, the N most differentially expressed genes are selected and are called pairwise differentially expressed genes (DEGs). In certain examples, the DEGs are identified and ranked by t-test, Mann-Whitney U test, or other tests that compare mean and median between 2 or more groups.

In certain embodiments, N is between 20 and 80. In certain embodiments, N is about 30, 40, 50, 60, 70, 80, 90 or 100. In certain embodiments, N is around 50.

In certain embodiments, the gene expression profile described herein is obtained by transcriptome RNA sequencing or microarray. In certain embodiments, the gene expression profile described herein is obtained from the cancer genome atlas (TCGA) dataset.

In certain embodiments, the method described herein is computer-implemented, i.e., the method is carried out in a computer, e.g., a computer program executed by a CPU. A computer, as used herein, refers to a device (for general or specific purposes) that can be programmed to perform a set of arithmetic or logical operations automatically. Computers, as used herein, include without limitation personal computers, workstations, servers, mainframes and supercomputers. The computer can be a stand-alone system, networked system or a virtual machine residing in a computing cloud. The methods described herein can be implemented with multithreading or other parallel computing methods.

As used herein, the term "cancer" refers to a group of diseases involving abnormal cell growth and division. In general, cancers can be categorized according to the tissue or organ from which the cancer is located or originated and morphology of cancerous tissues and cells. As used herein, cancer types include, without limitation, acute lymphoblastic leukemia (ALL), acute myeloid leukemia, adrenocortical carcinoma, anal cancer, astrocytoma, childhood cerebellar or cerebral, basal-cell carcinoma, bile duct cancer, bladder cancer, bone tumor, brain cancer, cerebellar astrocytoma, cerebral astrocytoma/malignant glioma, ependymoma, medulloblastoma, supratentorial primitive neuroectodermal tumors, visual pathway and hypothalamic glioma, breast cancer, Burkitt's lymphoma, cervical cancer, chronic lymphocytic leukemia, chronic myelogenous leukemia, colon cancer, emphysema, endometrial cancer, ependymoma, esophageal cancer, Ewing's sarcoma, retinoblastoma, gastric (stomach) cancer, glioma, head and neck cancer, heart cancer, Hodgkin lymphoma, islet cell carcinoma (endocrine pancreas), Kaposi sarcoma, kidney cancer (renal cell cancer), laryngeal cancer, leukaemia, liver cancer, lung cancer, neuroblastoma, non-Hodgkin lymphoma, ovarian cancer, pancreatic cancer, pharyngeal cancer, prostate cancer, rectal cancer, renal cell carcinoma (kidney cancer), retinoblastoma, Ewing family of tumors, skin cancer, stomach cancer, testicular cancer, throat cancer, thyroid cancer, vaginal cancer.

In certain embodiments, the cancer type described herein is colon adenocarcinoma (COAD), rectum adenocarcinoma (READ), lung adenocarcinoma (LUAD), lung squamous cell carcinoma (LUSC), head and neck squamous cell carcinoma (HNSC), liver hepatocellular carcinoma (LIHC), or pancreatic adenocarcinoma (PAAD).

The term "cancer sample" used herein encompasses any sample obtained, directly or indirectly, from a cancer patient. A sample can, by way of non-limiting example, include cerebrospinal fluid (CSF), blood, amniotic fluid, sera, urine, feces, epidermal sample, skin sample, cheek swab, sperm, amniotic fluid, cultured cells, bone marrow sample and/or chorionic villi. Cancer cell cultures can also be used as samples. A cancer sample can also be, e.g., a sample obtained from any organ or tissue (including a surgical removal, biopsy or autopsy specimen), can comprise cells (whether primary cells or cultured cells), medium conditioned by any cell, tissue or organ, tissue culture. In some embodiments, biological samples suitable for the invention are samples which have been processed to release or otherwise make available a nucleic acid for detection as described herein. Suitable biological samples may be obtained from a stage of life such as a fetus, young adult, adult (e.g., pregnant women), and the like. Fixed or frozen tissues also may be used.

In certain embodiments, the cancer sample used herein is not a cancer cell line. The term "cancer cell line" used herein refers to a population of cells isolated from a cancer patient and being cultured and immortalized in vitro such that the cells have evaded normal cellular senescence and can proliferate definitely. In certain embodiments, the cancer sample used herein is derived directly from a cancer patient, i.e., without cell culture. In certain embodiments, the cancer sample is a surgical removal sample or biopsy sample.

In certain embodiments, the cancer sample used herein is derived from a patient derived xenograft (PDX). "Patient derived xenograft," as used herein, refers to a graft of tissue or cells taken from a human patient donor, and grafted into an animal model (e.g., mouse, rat, rabbit, etc.). In some embodiments, the xenograft tissue or cells are tumor tissue or cells, or cancerous tissue or cells. In some embodiments, the xenograft is pre-treated before grafting into the animal model. The term "pre-treated" when refers to tissue, generally relates to any processing methods known in the art to treat a tissue before its engraftment, such as washing, homogenization, re-suspension and mixing with a solution (e.g., saline, PBS etc.) or a matrix (e.g., collagen). The term "pre-treated" when refers to cells, includes any processing methods known in the art to treat cells before its engraftment, such as culture, sub-culture, activating, treatment with an agent, centrifugation, re-suspension, filtration, and mixing with a solution (e.g., saline, PBS etc.) or a matrix (e.g., collagen). After grafted with xenograft, the animal model is allowed sufficient time to develop a lesion of the human disease for further use. The xenograft can be grafted to the animal model using any suitable methods known in the art, for example, by grafting cells subcutaneously, intraperitoneally, or intravenously through injection; or alternatively, by implanting a fraction of tissue through surgery. In some embodiments, the xenografts are tumor cells or cancerous cells, and are grafted to the animal model through subcutaneously injection.

In certain embodiments, the method described above further comprises diagnosing a cancer based on the expression of the pairwise DEGs. The term "diagnosing" or "diagnosis" means the identification of the nature of a disease, e.g., a cancer. The diagnosis of cancer can be carried out using the method described herein alone or in combination with other methodologies, e.g., methods based on histopathology. In one embodiment, to diagnose a cancer of a first type rather than a second type, a sample for a subject suspected of having a first cancer type is obtained. The gene expression levels of the pairwise DEGs between the first cancer type and the second cancer type are assayed, based on which whether the cancer is the first type can be determined.

In another aspect, the present disclosure provides a method comprising:

obtaining a first gene expression profile of a first cancer sample having a first cancer type;

obtaining a second gene expression profile of a second cancer sample having a second cancer type, wherein the second cancer type is different from the first cancer type;

obtaining a third gene expression profile of a third cancer sample having a third cancer type, wherein the third cancer type is different from the first and the second cancer type;

comparing said first gene expression profile with said second gene expression profile;

selecting $N_1$ genes that are most differentially expressed in the first and the second gene expression profiles to generate first pairwise DEGs, wherein $N_1$ is an integer between 10 and 100;

comparing said first gene expression profile with said third gene expression profile;

selecting $N_2$ genes that are most differentially expressed in the first and the third gene expression profiles to generate second pairwise DEGs, wherein $N_2$ is an integer between 10 and 100;

comparing said second gene expression profile with said third gene expression profile;

selecting $N_3$ genes that are most differentially expressed in the second and the third gene expression profiles to generate third pairwise DEGs, wherein $N_3$ is an integer between 10 and 100; and generating a signature genes that comprises the first, second and third pairwise DEGs.

In certain embodiments, $N_1=N_2=N_3$. In one embodiment, $N_1$, $N_2$ and $N_3$ are around 50.

In one embodiment, the signature genes are generated by combining the first, second and third pairwise DEGs. It can be understood that the first, second and third pairwise DEGs may have overlap so that the number of signature genes may be less than the sum of $N_1$, $N_2$, and $N_3$.

The method described above can be extended to analyzing data set with more than 3 cancer types. For example, for a dataset with P cancer types, n DEGs for each pairwise comparison between cancer types. In a global comparison, a total of $P(P-1)/2$ pairwise DEGs can be generated. A signature genes can be obtained by combining all $P(P-1)/2$ pairwise DEGs. The number of the signature genes is capped at $P(P-1)n/2$ but usually fewer due to overlapping of the pairwise DEGs. Samples in any cancer type pair can be distinguished by their n DEGs, while other DEGs that are capped at $(P-1)(P-2)n/2$ but usually fewer due to overlapping, can be viewed as background noise.

In certain embodiments, the signature genes have m genes, wherein m is an integer between 5 to 5000. In certain embodiments, m is between 100-1000. In certain embodiments, m is between 100-500.

In certain embodiments, the method described above further comprises diagnosing a cancer based on the expression of the signature genes. In one embodiment, to diagnose a cancer, a sample from a subject suspected of having a cancer is obtained. The expression levels of the signature genes are assayed (e.g., through gene expression profiling using microarray or RNA-seq), based on which the nature of the cancer can be identified.

In yet another aspect, the present disclosure provides a method for treating a cancer in a subject, comprising diagnosing the cancer type in the subject by the method as described herein, and administering a drug that can effectively treat the cancer type.

In yet another aspect, the present disclosure provides a method for treating a first cancer type in a subject, wherein the first cancer type has the same expression profile of pairwise DEGs as a second cancer type, the method comprising administering to the subject a drug that can effectively treat the second cancer type.

In one embodiment, the first cancer type is colon adenocarcinoma (COAD), and the second cancer type is rectum adenocarcinoma (READ). In one embodiment, the first cancer type is rectum adenocarcinoma (READ), and the second cancer type is colon adenocarcinoma (COAD).

Drugs used for treating colon cancer include without limitation, Bevacizumab (brand name AVASTIN®), Capecitabine (brand name XELODA®), Cetuximab (brand name ERBITUX®), 5-FU, Fluorouracil Injection, Irinotecan hydrochloride (brand name CAMPTOSAR®), Leucovorin Calcium, Oxaliplatin (brand name ELOXATIN®), Panitumumab (brand name VECTIBIX®), Ramucirumab (brand name CYRAMZA®), Regorafenib (brand name STIVARGA®), Trifluridine and Tipiracil hydrochloride (brand name LONSURF®), WELLCOVORIN®, Ziv-aflibercept (brand name ZATRAP®).

Drugs used for treating rectal cancer include without limitation, Bevacizumab (brand name AVASTIN®), Capecitabine (brand name XELODA®), Cetuximab (brand name ERBITUX®), 5-FU, Fluorouracil Injection, Irinotecan hydrochloride (brand name CAMPTOSAR®), Leucovorin Calcium, Oxaliplatin (brand name ELOXATIN®), Panitumumab (brand name VECTIBIX®), Ramucirumab (brand name CYRAMZA®), Regorafenib (brand name STIVARGA®), Trifluridine and Tipiracil hydrochloride (brand name LONSURF®), WELLCOVORIN®, Ziv-aflibercept (brand name ZATRAP®).

In one embodiment, the first cancer type is neck squamous cell carcinoma (HNSC), and the second cancer type is lung squamous cell carcinoma (LUSC). In one embodiment, the first cancer type is lung squamous cell carcinoma (LUSC), and the second cancer type is neck squamous cell carcinoma (HNSC).

Drugs used for treating head and neck cancer include without limitation, Bleomycin (brand name BLENOXANE®), Cetuximab (brand name ERBITUX®), Docetaxel (brand name TAXOTERE®), Hydroxyurea (brand name HYDREA®), Methotrexate (brand name ABITREXATE®, METHOTREXATE LPF™, MEXATE®, MEXATE-AQ™, FOLEX®, FOLEX PFS™), Pembrolizumab (KEYTRUDA®).

Drugs used for treating lung cancer include without limitation, Afatinib dimaleate (brand name Gilotrif®), Alectinib (brand name Alecensa®), Bevacizumab (brand name Avastin®), Carboplatin (brand name Paraplatin®), Ceritinib (brand name Zykadia®), Docetaxel (brand name Taxotere®), Erlotinib (brand name Tarceva®), Everolimus (brand name Afinitor®), Gefitinib (brand name Iressa®), Gemcitabine Hydrochloride (brand name Gemzar®), Mechlorethamine hydrochloride (brand name Mustargen®), Methotrexate (brand name Abitrexate®, Methotrexate-AQ™, Folex®, Folex PFS™), Necitumumab (brand name Portrazza®), Nivolumab (brand name Opdivo®), Osimertinib (brand name Tagrisso®), Paclitaxel (brand name Abraxane®, Taxol®), Pembrolizumab (brand name Keytruda®), Pemetrexed disoldium (brand name Alimta®), Ramucirumab (brand name Cyramza®), Vinorelbine Tartrate (brand name Navelbine®), Xalkori®.

The following examples are presented to illustrate the present invention. They are not intended to limiting in any manner.

Example 1

This example shows the expression similarity within and between histopathological cancer types.

Materials and Methods

Engraftment and Molecular Characterization of Xenograft Tissues

Methods and parameters regarding xenograftment of patient tissues (Crown Bioscience SPF facility) have been described previously (Yang M et al., "Overcoming erlotinib resistance with tailored treatment regimen in patient-derived xenografts from naive Asian NSCLC patients" International journal of cancer (2013) 132(2):E74-84; Zhang L et al., "A subset of gastric cancers with EGFR amplification and overexpression respond to cetuximab therapy" Sci Rep (2013) 3:2992; Jiang J et al., "Comprehensive characterization of chemotherapeutic efficacy on metastases in the established gastric neuroendocrine cancer patient derived xenograft model" Oncotarget (2015) 6(17):15639-51; Bladt F et al., "The c-Met Inhibitor MSC2156119J Effectively Inhibits Tumor Growth in Liver Cancer Models" Cancers (Basel) (2014) 6(3):1736-52). For transcriptome sequencing of PDX tumor tissues, snap frozen samples were used to extract RNAs per method described previously (Yang M et al., "Overcoming erlotinib resistance with tailored treatment regimen in patient-derived xenografts from naive Asian NSCLC patients" International journal of cancer (2013) 132(2):E74-84; Zhang L et al., "A subset of gastric cancers with EGFR amplification and overexpression respond to cetuximab therapy" Sci Rep (2013) 3:2992). The purity and integrity of the RNA samples were ensured by Agilent Bioanalyzer prior to RNA sequencing. Only RNA samples with RIN>7 and 28S/18S>1 were proceeded for library construction and RNA sequencing. RNA samples (mouse component <50%) were used for transcriptome sequencing by certified Illumina HiSeq platform service providers (BGI, Wuhan, China). Transcriptome sequencing was generally performed at 6 GB, PE125 on Illumina HiSeq2500 platform or equivalent. For Affymetrix U219 GeneChip profiling, RNA samples from tumors were processed and assayed as previously described (Yang M et al., "Overcoming erlotinib resistance with tailored treatment regimen in patient-derived xenografts from naive Asian NSCLC patients" International journal of cancer (2013) 132(2):E74-84; Zhang L et al., "A subset of gastric cancers with EGFR amplification and overexpression respond to cetuximab therapy" Sci Rep (2013) 3:2992). Standard immunohistochemistry (IHC) was used to analyze selected FFPE PDX tumor tissues as described previously (Yang M et al., "Overcoming erlotinib resistance with tailored treatment regimen in patient-derived xenografts from naive Asian NSCLC patients" International journal of cancer (2013) 132(2):E74-84; Zhang L et al., "A subset of gastric cancers with EGFR amplification and overexpression respond to cetuximab therapy" Sci Rep (2013) 3:2992). The antibodies used for IHC were: anti-human monoclonal antibody TTF1 (ZM-0250, mouse), CDX2 (ZA-0520, rabbit), CK7 (ZM-0071, mouse), CK20 (ZM-0075, mouse), are all from Zhongsan JinQiao, China.

TCGA Datasets and CCLE Datasets

Level 3 TCGA RNA-seq data for seven cancer types (COAD, READ, LUAD, LUSC, HNSC, LIHC, PAAD) were downloaded from the TCGA Data Portal (February 2015 Release). We only used the RNA-seq data generated by the Illumina HiSeq platform and processed by the RNAseqV2 pipeline, which used MapSplice for read alignment and RSEM for quantification. The TCGA dataset contains 285 COADs, 94 READs, 515 LUADs, 501 LUSCs, 519 HNSCs, 371 LIHCs, and 178 PAADs.

The cancer cell line gene expression data were downloaded from the CCLE data portal (October 2012 Release). The expression was profiled on Affymetrix U133Plus2 GeneChip. The raw Affymetrix CEL files were converted into gene expression values by the Robust Multi-array Average (RMA) algorithm with a custom CDF file (ENTR-EZF v15). A total of 210 cell lines were used, including 47 CRADs, 52 LUADs, 28 LUSCs, 30 HNSCs, 25 LIHCs, and 28 PAADs (Table 1).

Bioinformatics Analysis of PDX Transcriptome Sequencing Data

Gene expression in PDXs was profiled by both Affymetrix U219 GeneChip and RNA-seq per methods previously described (Yang M et al., "Overcoming erlotinib resistance with tailored treatment regimen in patient-derived xenografts from naive Asian NSCLC patients". International journal of cancer (2013) 132(2):E74-84; Chen D et al., "A set of defined oncogenic mutation alleles seems to better predict the response to cetuximab in CRC patient-derived xenograft than KRAS 12/13 mutations" Oncotarget (2015) 6(38):40815-21). The Affymetrix CEL files were processed using the same method for CCLE data. The RNA-seq raw data were first cleaned up by removing mouse reads mapped to a mouse reference genome (UCSC MM9). The average mouse content is about 10%. Gene expression was estimated using the TCGA RNAseqV2 pipeline. A total of 175 PDXs with Affymetrix U219 data were used including 58 CRADs, 11 LUADs, 40 LUSCs, 10 HNSCs, 24 LIHCs, and 32 PAADs. A total of 241 PDXs with RNA-seq data were used including 82 CRADs, 12 LUADs, 54 LUSCs, 14 HNSCs, 30 LIHCs, and 49 PAADs.

Comparison of Transcriptome Expression Datasets

The edgeR package (Robinson M D and Smyth G K, "Small-sample estimation of negative binomial dispersion, with applications to SAGE data" Biostatistics (2008) 9(2): 321-32) (version 3.10.2) from Bioconductor (version 3.1) was used to analyze the TCGA RNA-seq data. Genes with at least one count per million in at least 94 samples, the smallest of all 7 cancers, were kept. Differentially expressed genes (DEGs) were identified and ranked by the exactTest function. For the 7 TCGA cancer types, 21 pairwise comparisons were performed, and certain numbers of top DEGs were retained. Expression values of DEGs were normalized to have zero mean and unit variance, and used to calculate Pearson correlation coefficients between samples. In FIG. 1A-D, 94 samples for each of the 7 cancers in TCGA were used by random sampling. For the other 3 datasets, the expression values were normalized as well in calculating within-type and between-type Pearson correlation coefficients. All expression values were in logarithmic scale in the correlation calculation and heatmaps. Graphs in FIG. 4A-D were generated using the plotMDS function in the edgeR package (version 3.10.2), and the first two leading log-fold-changes (logFCs) were used at the 2 axes.

Results

Figure 5A:
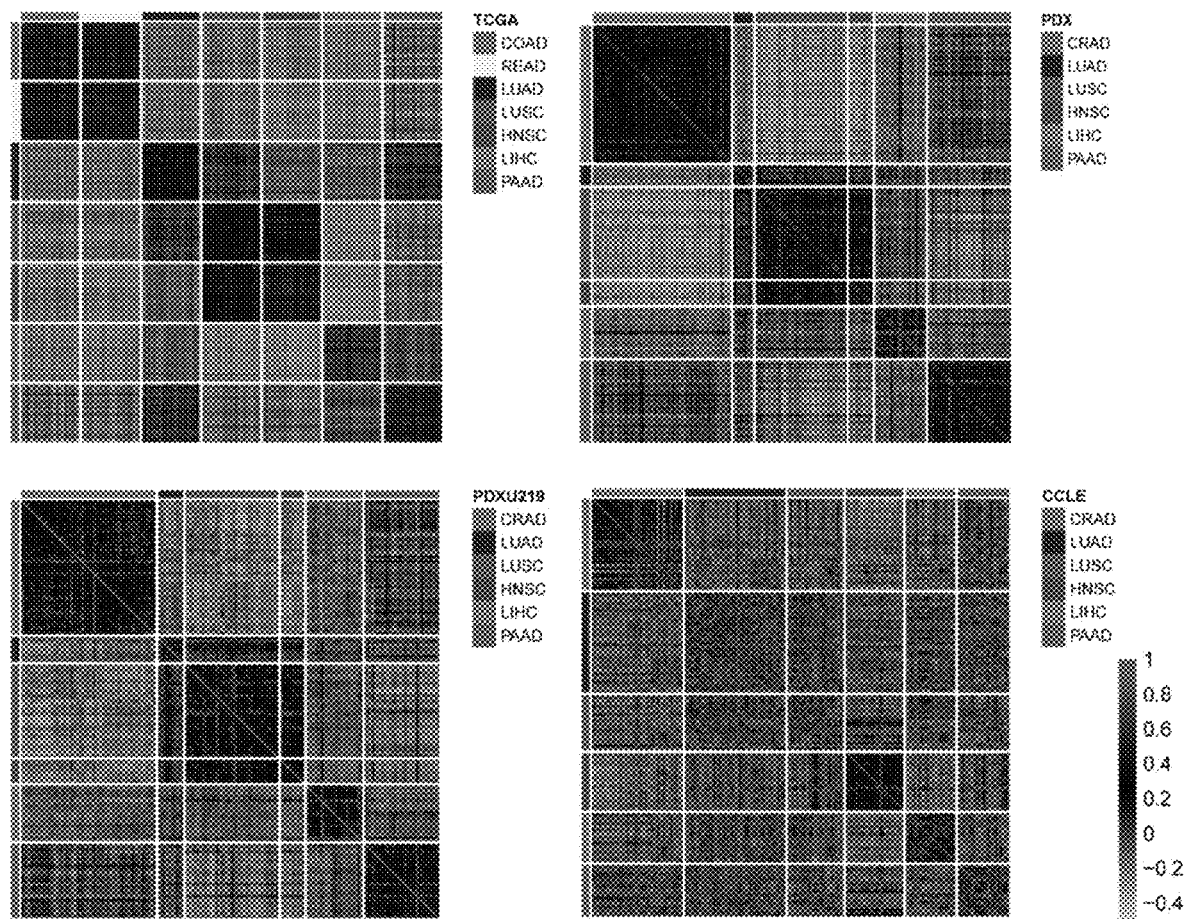
FIG. 5A illustrates the comparison of gene expression for TCGA patient samples within and between cancer types when the number of pairwise DEGs is 3000, at which there are 6651 unique genes, about one-third of genes profiled. The gene expression for TCGA patient samples was profiled by RNA-Seq, PDXs profiled by RNA-seq (PDX), PDXs profiled by microarray (PDXU219), and cancer cell lines profiled by microarray (CCLE). In the heatmaps, Pearson correlation coefficient between two samples is color coded; the length of a color bar on the top or left is proportional to sample size within a dataset.
Figure 5B:
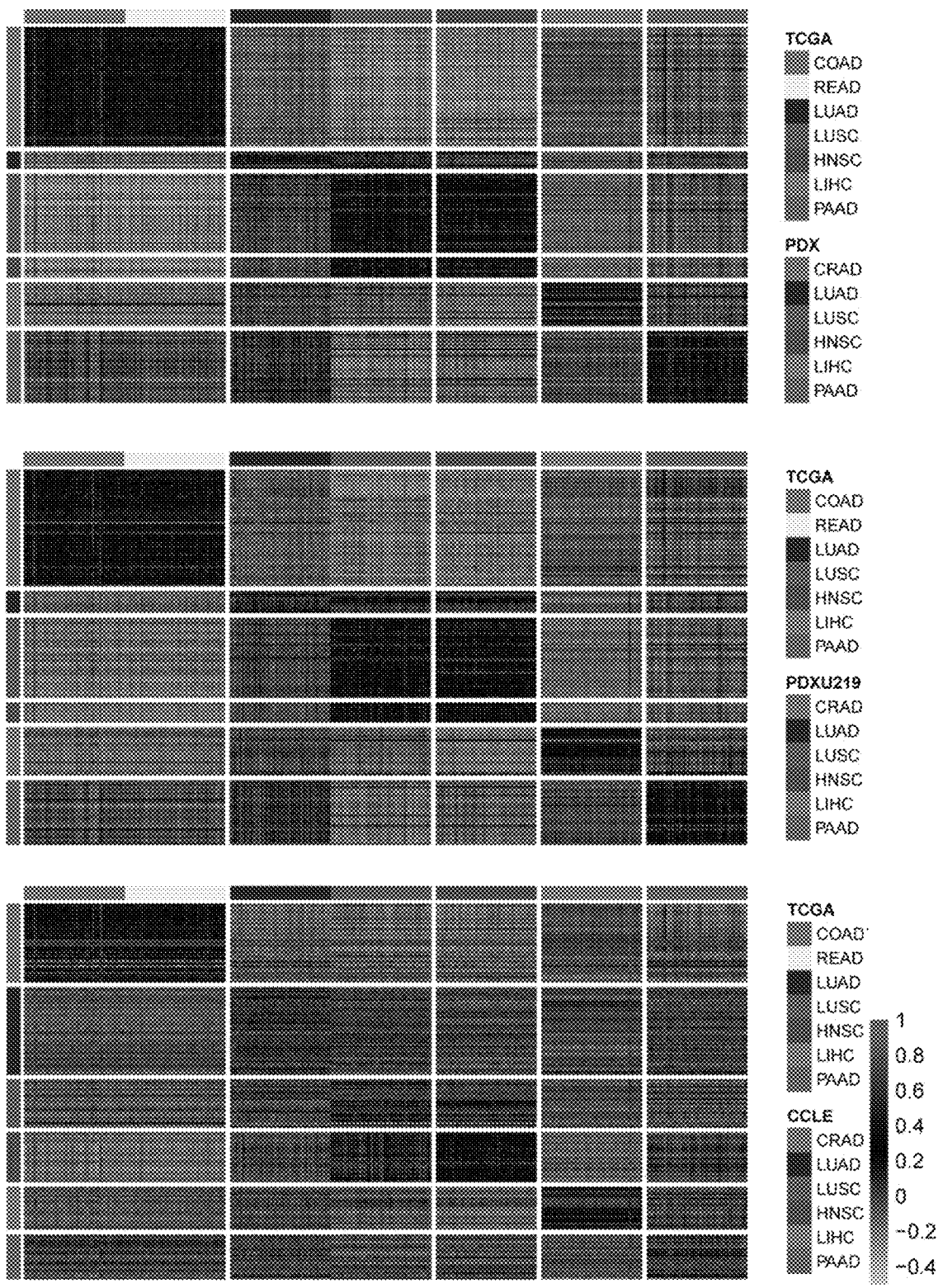
FIG. 5B illustrates the comparison of gene expression between TCGA and the other 3 datasets when the number of pairwise DEGs is 3000, at which there are 6651 unique genes, about one-third of genes profiled. In the heatmaps, Pearson correlation coefficient between two samples is color coded; the length of a color bar on the top or left is proportional to sample size within a dataset.

We set out to inquire whether cancers of the same histopathological diagnosis have similar expression profiles, as compared against different histopathology types. We examined 4 transcriptome expression datasets: a) the TCGA transcriptome sequencing (RNA-seq) dataset for patient tumor samples obtained through surgical removal or biopsy ("Comprehensive molecular characterization of gastric adenocarcinoma" Nature (2014) 513(7517):202-9; "Comprehensive genomic characterization defines human glioblastoma genes and core pathways" Nature (2008) 455 (7216):1061-8; Ge L et al., "Integrated analysis of gene expression profile and genetic variations associated with ovarian cancer" Eur Rev Med Pharmacol Sci (2015) 19(14): 2703-10); b) the RNA-seq dataset (referred to as PDX) and c) the microarray dataset (referred to as PDXU219) for patient derived xenograft of various diseases; d) the microarray dataset for cancer cell lines from the Cancer Cell Line Encyclopedia (CCLE) project (Barretina J et al., "The Cancer Cell Line Encyclopedia enables predictive modelling of anticancer drug sensitivity" Nature (2012) 483 (7391):603-7). First of all, we aimed at establishing an algorithm to define human disease types by transcriptome expression, postulating that distinct gene expression signature is the molecular hallmark of both normal and tumor tissues (or types as defined). To this end, we performed 21 pairwise comparisons of transcriptome expression for 7 TCGA cancers: colon adenocarcinoma (COAD), rectum adenocarcinoma (READ), lung adenocarcinoma (LUAD), lung squamous cell carcinoma (LUSC), head and neck squamous cell carcinoma (HNSC), liver hepatocellular carcinoma (LIHC), and pancreatic adenocarcinoma (PAAD). For each pairwise comparison, we retained the same number of the most differentially expressed genes (DEGs), ranked by p-values from the exactTest function in the edgeR package in R (see Methods). The total DEGs, by summing up from all pairwise comparisons with redundancy removal, were used to calculate the within-type (histopathology type) and between-type correlation coefficients for the TCGA dataset. The correlation coefficients were used to quantify cancer similarity (FIG. 1A). A total of 686 genes, which is the non-redundant set when the number of pairwise DEGs is 50, are used in the illustration in FIG. 1A-D. The similarity patterns hold true for other numbers of DEGs, up to whole transcriptome (FIG. 5A-B). This pairwise comparison approach is intended to minimize bias toward certain cancer types, as opposed to the methods that select genes by simultaneous-comparing all cancer types, e.g. one-way ANOVA.

Figure 2A:
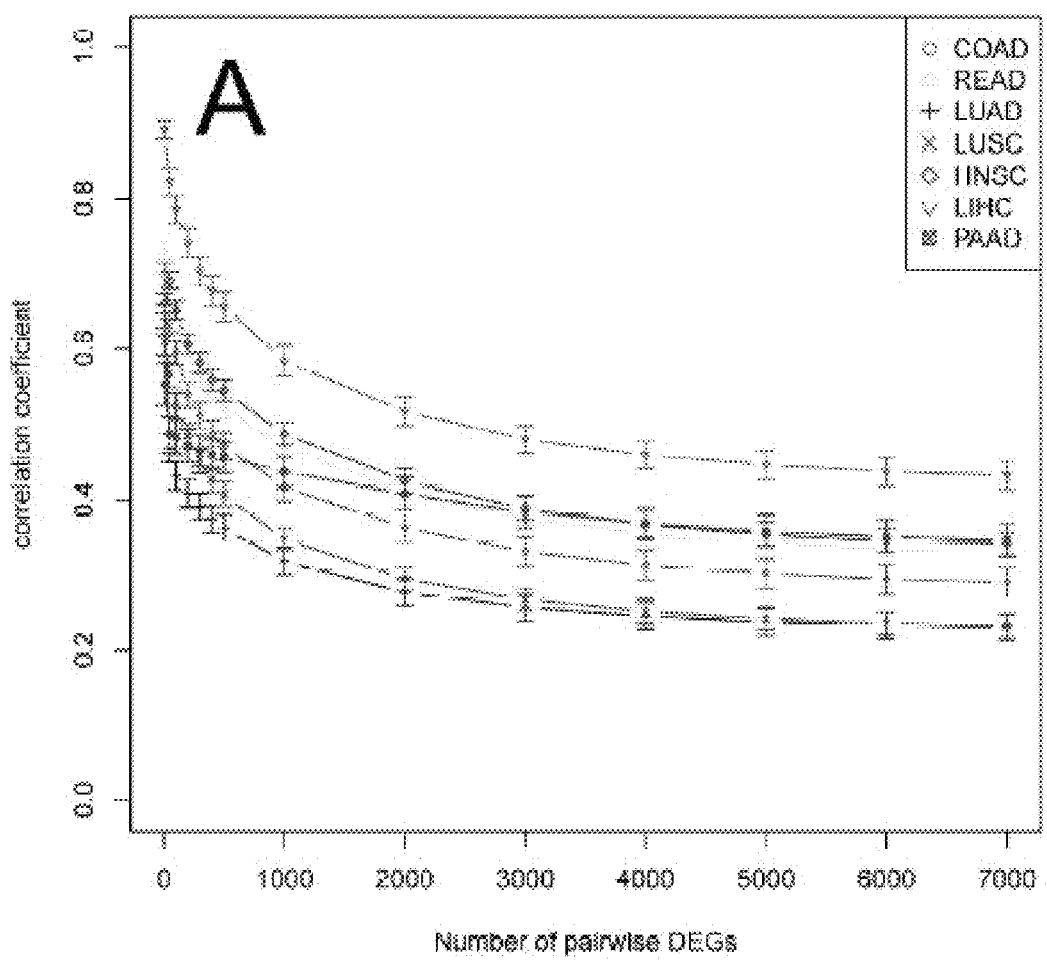
FIG. 2A illustrates the gene expression similarity within each cancer type at different numbers of pairwise DEGs in TCGA dataset. For each cancer type in the dataset, Pearson correlation coefficients for all pairs of samples were calculated based on the normalized gene expression values. Values are the mean and SEM.
Figure 6:
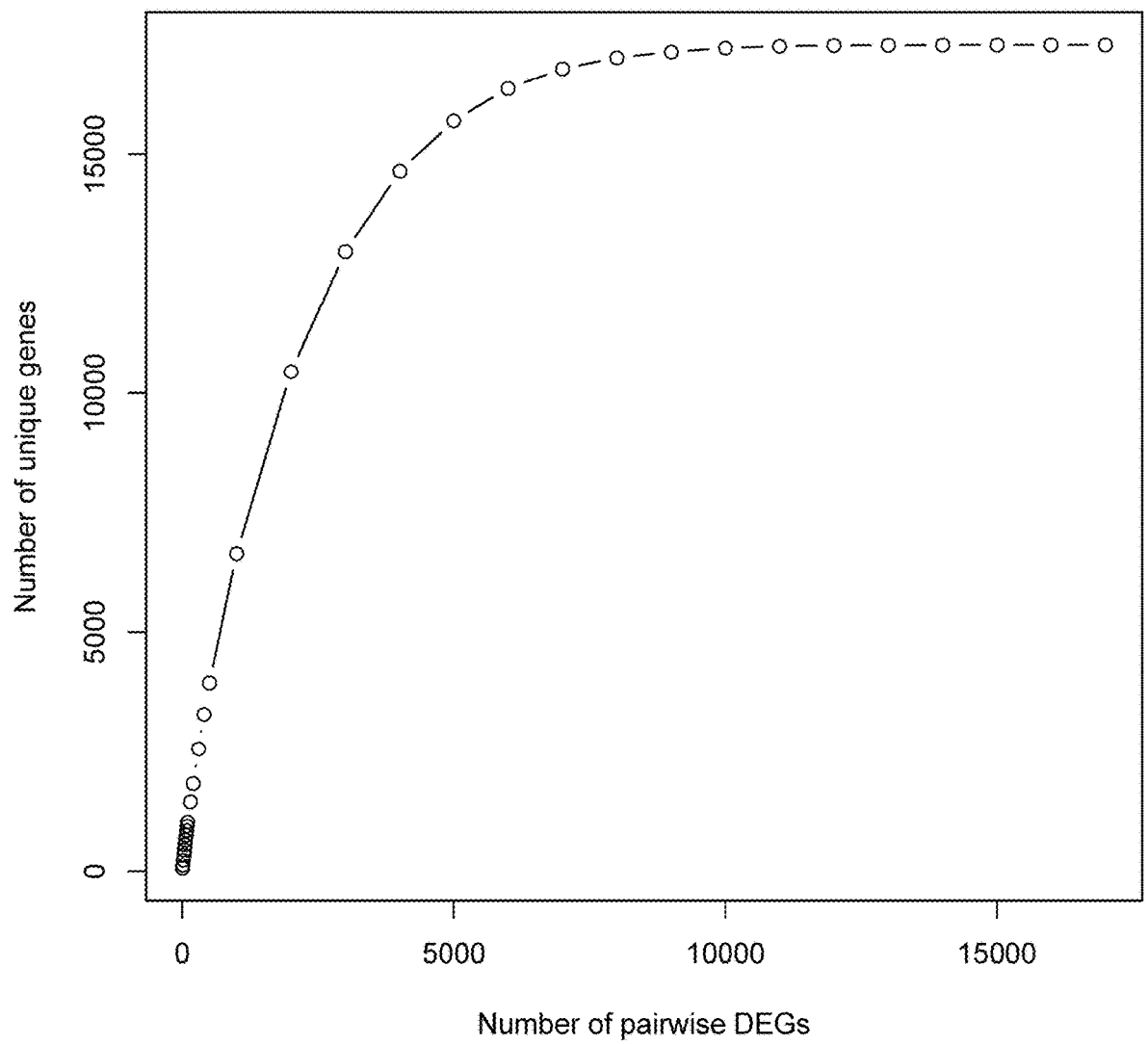
FIG. 6 illustrates the relationship between number of unique genes and number of pairwise DEGs in the TCGA dataset. When the number of pairwise DEGs is 50, there are 686 unique genes. When the number of pairwise DEGs reaches 7000, there are 16798 unique genes, about 97.1% of the 17288 genes eligible for pairwise comparisons in the TCGA dataset.

We observed that the within-type correlation coefficients initially decrease rapidly then stabilize for all cancer types in TCGA as the number of DEGs increases (FIG. 2A), because relatively few new genes are added at high numbers of DEGs (FIG. 6). When the number of pairwise DEGs reaches 7000, there are 16798 unique genes, about 97.1% of the 17288 genes eligible for pairwise comparison in the TCGA dataset. The relatively high within-type coefficients (as opposed to between-type coefficients, see below) demonstrate cancer type specificity, which is largely in accordance with histopathology classification. Meanwhile, the within-type correlation coefficients at any given DEGs vary among cancer types, reflecting their different degree of homogeneity. For example, LIHC seems to be much more homogeneous than other types.

Figure 2B:
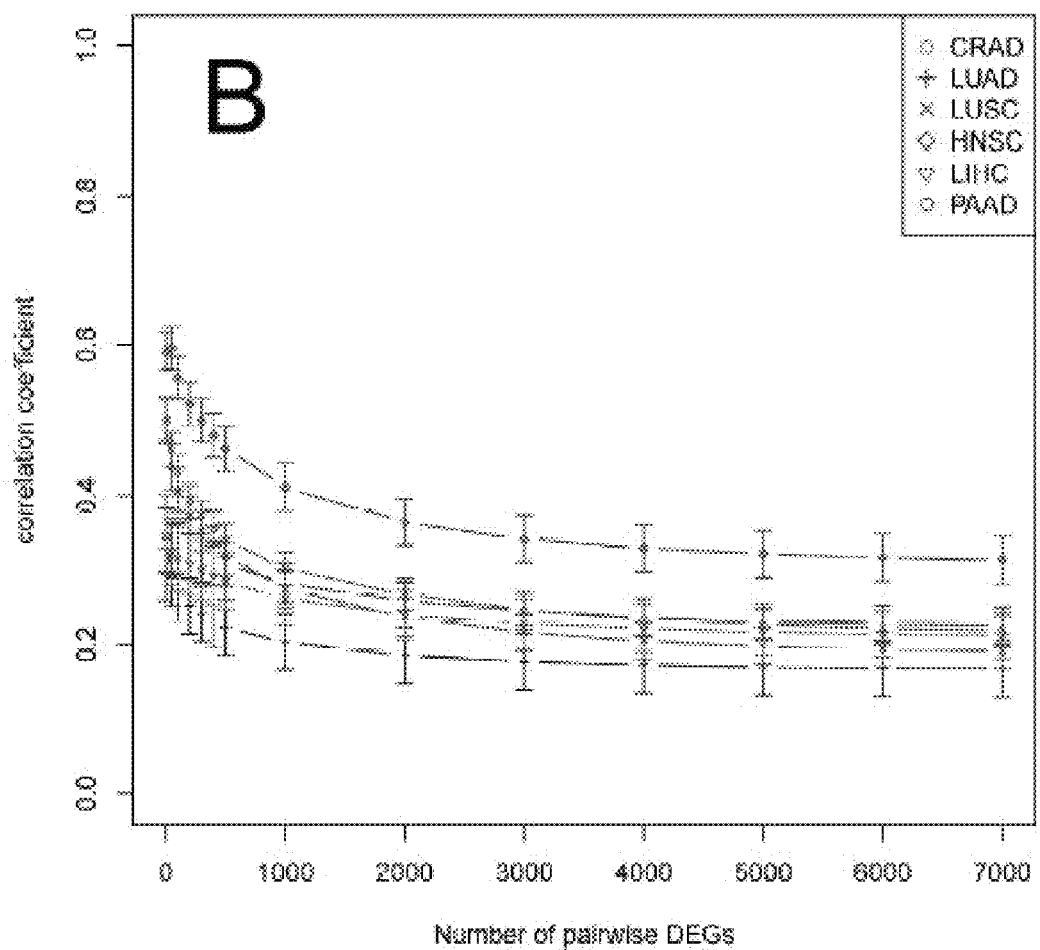
FIG. 2B illustrates the gene expression similarity within each cancer type at different numbers of pairwise DEGs in PDX dataset. For each cancer type in the dataset, Pearson correlation coefficients for all pairs of samples were calculated based on the normalized gene expression values. Values are the mean and SEM.
Figure 2C:
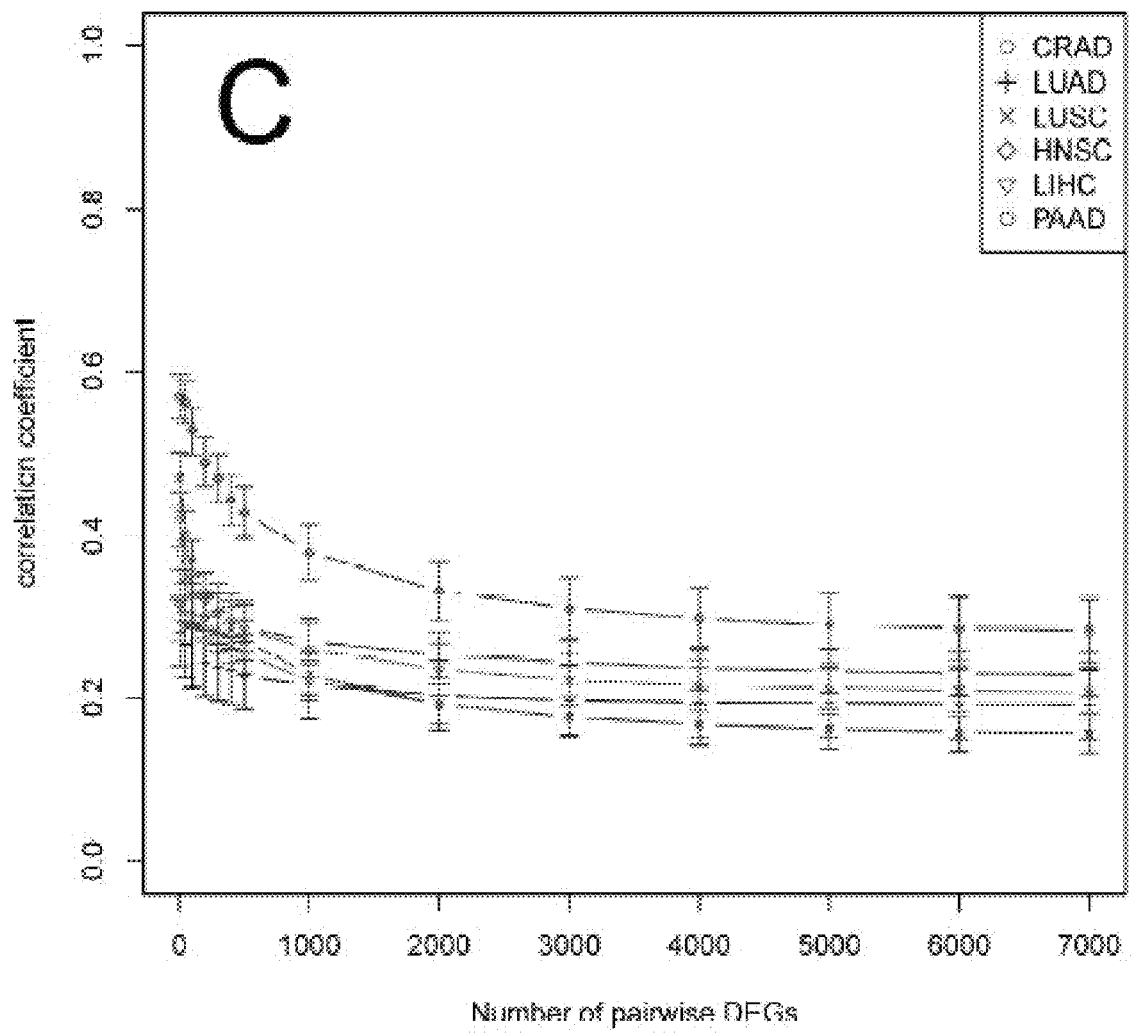
FIG. 2C illustrates the gene expression similarity within each cancer type at different numbers of pairwise DEGs in PDXU219 dataset. For each cancer type in the dataset, Pearson correlation coefficients for all pairs of samples were calculated based on the normalized gene expression values. Values are the mean and SEM.

Patient derived xenograft diseases are largely reflective of original patient diseases per histopathology, cell types, differentiation phenotypes (Tentler J J et al., "Patient-derived tumour xenografts as models for oncology drug development" Nat Rev Clin Oncol (2012) 9(6):338-50; Ding L et al., "Genome remodelling in a basal-like breast cancer metastasis and xenograft" Nature (2010) 464(7291):999-1005; Yang M et al., "Overcoming erlotinib resistance with tailored treatment regimen in patient-derived xenografts from naive Asian NSCLC patients". International journal of cancer (2013) 132(2):E74-84; Zhang L et al., "A subset of gastric cancers with EGFR amplification and overexpression respond to cetuximab therapy". Sci Rep (2013) 3:2992; Akashi Y et al., "Histological advantages of the tumor graft: a murine model involving transplantation of human pancreatic cancer tissue fragments" Pancreas (2013) 42(8):1275-82), and also per molecular pathology as reported in a number of isolated studies (Tentler J J et al., "Patient-derived tumour xenografts as models for oncology drug development" Nat Rev Clin Oncol (2012) 9(6):338-50; Ding L et al., "Genome remodelling in a basal-like breast cancer metastasis and xenograft" Nature (2010) 464(7291):999-1005). To systematically investigate such relevance, we subsequently performed the correlation coefficient calculation for PDX (RNA-seq) and PDXU219 datasets (Yang M et al., "Overcoming erlotinib resistance with tailored treatment regimen in patient-derived xenografts from naive Asian NSCLC patients". International journal of cancer (2013) 132(2):E74-84; Zhang L et al., "A subset of gastric cancers with EGFR amplification and overexpression respond to cetuximab therapy". Sci Rep (2013) 3:2992) using the same DEGs derived from above TCGA pairwise comparisons. We made several observations (FIG. 2B, 2C): 1) In both datasets, we also observed an initial rapid decline in correlation coefficients, parallel to TCGA, with the increase in DEGs for all cancer types. This parallelism suggests that the same DEGs can also describe the cancer type specificity in PDXs as seen in TCGA, and thus shows the similarity between TCGA and PDX. 2) The overall values of correlation coefficient in PDXs are lower than those of TCGA and may be attributed to the two factors: PDXs lost some tumor specificity (further discussed below), and TCGA-centric approach likely leads to lower values in PDXs, especially at low numbers of DEGs. 3) The within-type correlation coefficients at any given DEGs vary significantly among PDX cancer types as well, reflecting different degree of homogeneity, as seen in TCGA. In particular, they may vary in values not in concordance with those in TCGA. For example, HNSC, but not LIHC, has the highest within-type correlation in PDXs. This suggests that a same cancer type can have different homogeneity in PDXs than in human, and such difference may be reflective of how far away PDXs have drifted from human tumors. But it may also be attributed to small sample sizes of HNSC PDXs (10 in the PDXU219 dataset and 14 in the PDX dataset). 4) It is worth noting that PDXU219 and PDX (RNA-seq) are almost parallel to each other with similar correlation coefficient values, implying a near equivalence of the two expression profiling approaches (FIG. 3). Overall, our observations agree with anecdotal reports that PDXs have similar molecular profiles as the tumors from which they were derived (5,6).

Figure 2D:
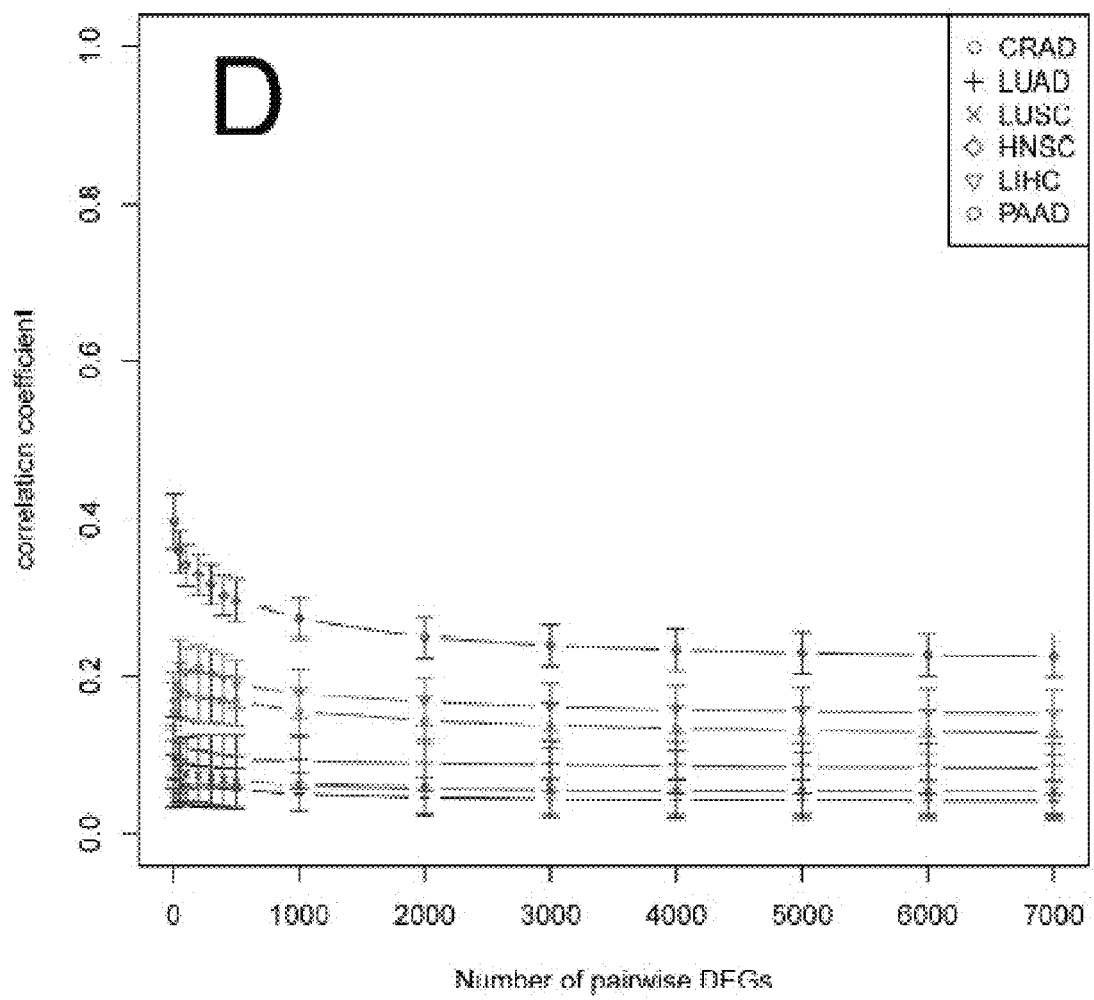
FIG. 2D illustrates the gene expression similarity within each cancer type at different numbers of pairwise DEGs in CCLE dataset. For each cancer type in the dataset, Pearson correlation coefficients for all pairs of samples were calculated based on the normalized gene expression values. Values are the mean and SEM.

Traditional cancer cell lines immortally grow in plastic flasks, usually clonally and with uniform morphology of undifferentiated phenotype. Many can grow in xenografts, but with compact and homogeneous morphology of little differentiation, which are all in sharp contrast to PDX. Therefore, they have been considered less relevant to human cancers, as compared to PDXs (5). Similarly, we also performed the within-type correlation coefficient calculation for the CCLE dataset. Interestingly, we barely observed any parallel decline of coefficients with the increase of DEGs for all cancer types except HNSC, suggesting the selected DEGs from TCGA have little relevance in CCLE (FIG. 2D). Furthermore, the within-type correlation coefficients are significantly lower in CCLE than in TCGA, PDX and PDXU219 (FIG. 3). It is unlikely that such decrease can be attributed to the TCGA-centric approach. The poor cancer type specificity observed in CCLE is consistent with the notion that cell lines deviate quite away from human cancers, both histopathologically and molecular pathologically. However, the within-type correlation coefficients, although low in general, do vary by types. For instance, HNSC cell lines show relatively higher coefficients (FIG. 2D). In summary, at any number of DEGs, the within-type correlation coefficients are highest in the TCGA dataset, lowest in the CCLE dataset, and intermediate yet close in the PDX and PDXU219 datasets.

Figure 3A:
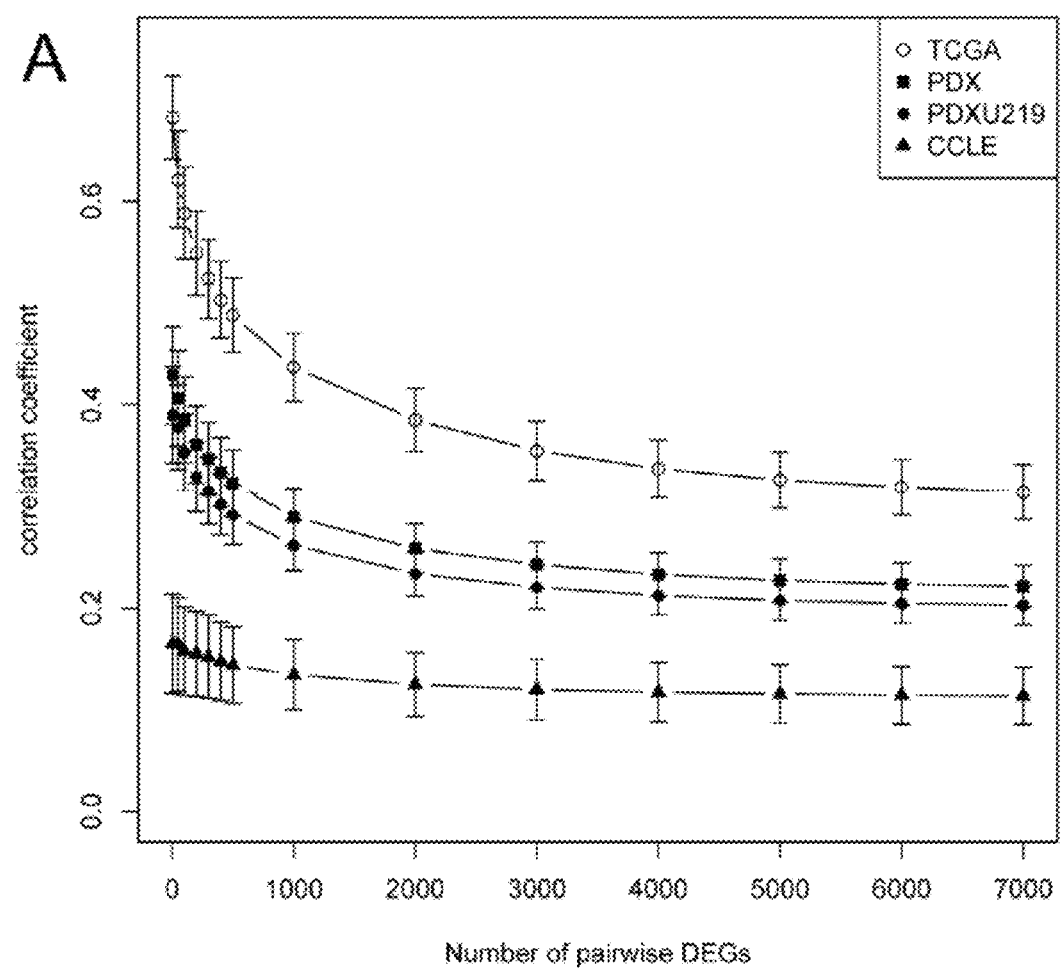
FIG. 3A illustrates the average within-type gene expression similarity at different numbers of pairwise DEGs in 4 datasets. Pearson correlation coefficients for all pairs of samples within the same cancer type in a dataset were calculated. Normalized gene expression values were used in calculations. Values are the mean and SEM.
Figure 3B:
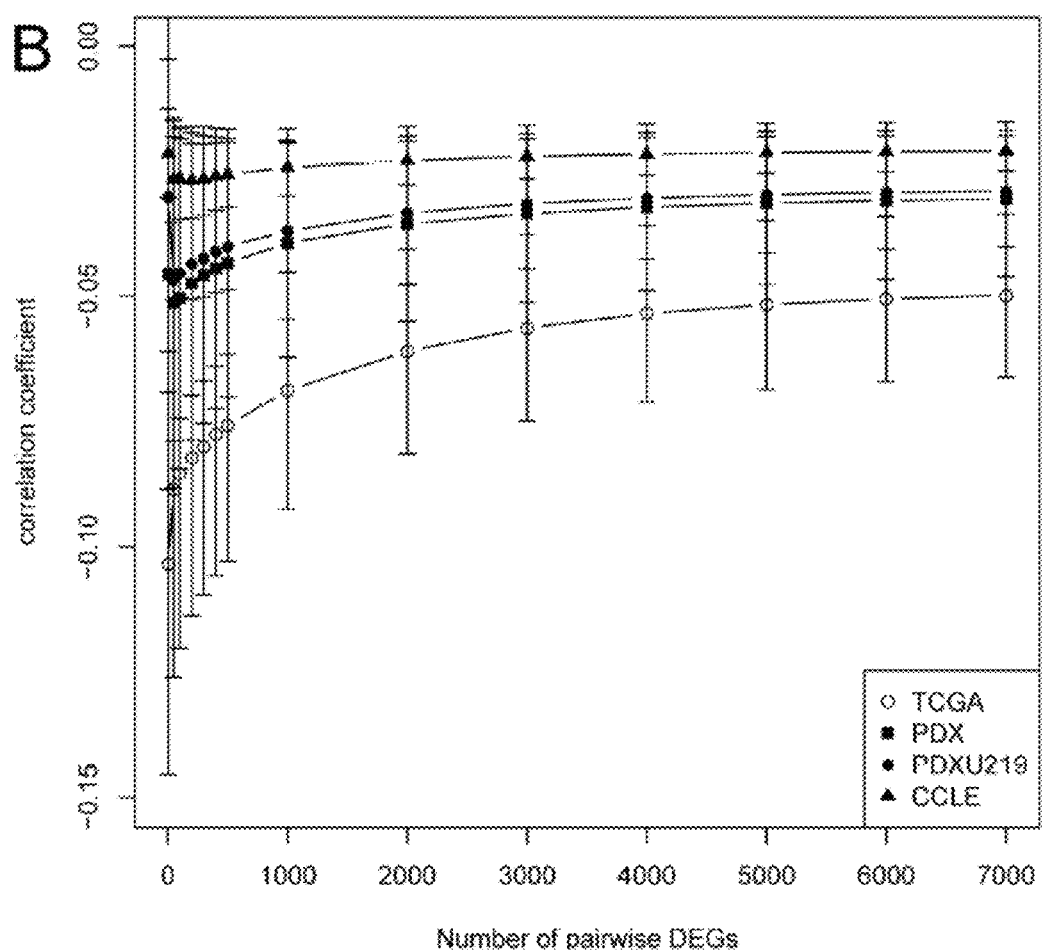
FIG. 3B illustrates the average between-type gene expression similarity at different numbers of pairwise DEGs in 4 datasets. Pearson correlation coefficients for all pairs of samples belonging to different cancer types in a dataset were calculated. Normalized gene expression values were used in calculations. Values are the mean and SEM.

Next, we performed the between-type correlation coefficient calculation using the same DEGs. We found that the coefficients are all negative and close to zero, reflecting that generally little similarity exists between different cancer types in all 4 datasets. Analogous to the within-type correlation, TCGA has the largest absolute values of correlation coefficient which exhibit an initial decline, PDX and PDXU219 have the intermediate values with parallel decline, while in CCLE, the values are smallest and flat (FIGS. 3A and 3B). In conclusion, patient tumors have the most pronounced cancer type specific gene expression profiles, and in general, have high correlation among the same histological cancer types. Patient derived xenografts (subcutaneously engrafted tumors) still maintain reasonable specificity, although not to the extent of human tumors, and are markedly better than cancer cell lines. With all the above analyses, we established a good degree of equivalence between two diagnosis methods, one based on histological morphology and tumor origin, and the other on transcriptome expression.

Example 2

This example illustrates the expression similarity between different cancer types and dissimilarity within same types.

The methods and materials are described in EXAMPLE 1.

Besides the within-type correlation and low between-type correlation in general as demonstrated in EXAMPLE 1, we also made some other interesting observations from patient tumors and PDXs (FIG. 1A-1D). First, colon adenocarcinoma (COAD) and rectum adenocarcinoma (READ) are virtually indistinguishable, suggesting that they could be essentially the same disease. Second, lung adenocarcinoma (LUAD) and lung squamous cell carcinoma (LUSC) have quite distinctive expression profiles even though both belong to non-small-cell lung carcinoma (NSCLC), consistent with fact that they have distinct morphology and pathogenesis. Third, HNSC is highly similar to LUSC by expression profiles, in accordance with the reported results in patient samples (Hoadley K A et al., "Multiplatform analysis of 12 cancer types reveals molecular classification within and across tissues of origin" Cell (2014) 158(4):929-44). It would be interesting to investigate the shared pathogenesis between these two squamous cell carcinomas.

Such observations again demonstrate the close relevance of PDX to human tumors. In contrast, in the CCLE dataset, LUAD and LUSC are not separable from each other. In fact, they have the lowest within-type correlation coefficients, being 0.067 and 0.080 when the number of pairwise DEGs is 50. Our pathology examination of lung cell line derived xenografts did not show morphological correlation within LUAD cell lines (e.g. A459, NCI-H1975, LU0682, LU6912, data not shown) and within LUSC cell lines (LU0357, data not shown). In the CCLE dataset, we did not observe high similarity between HNSC and LUSC, their between-type correlation coefficient is only 0.052 when the number of pairwise DEGs is 50, while at which the within-type correlation coefficient for HNSC is 0.36.

Example 3

This example illustrates the molecular pathology signature derived from TCGA for cancer classification.

The materials and methods are described in EXAMPLE 1.

Figure 4A:
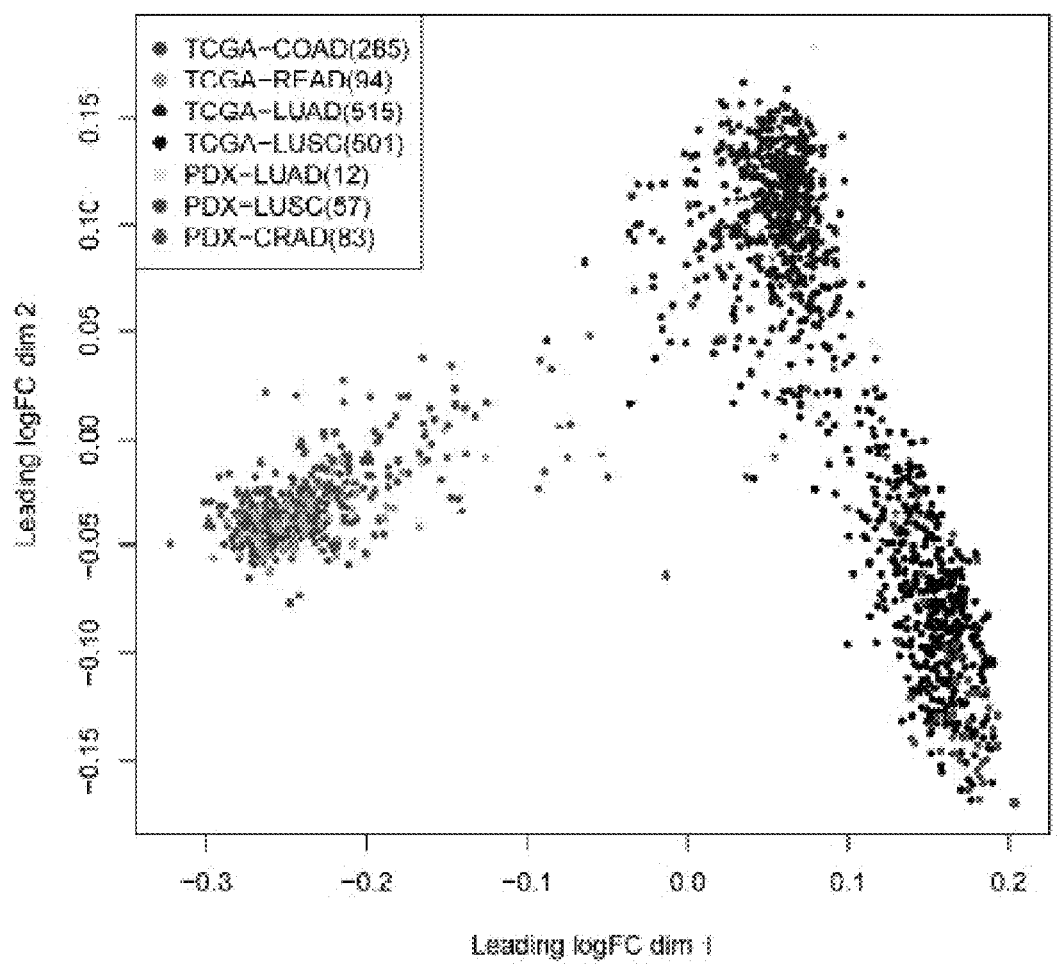
FIG. 4A illustrates multidimensional scaling (MDS) plots of colorectal cancer and lung cancer samples in TCGA and PDX. In the PDX dataset, 4 misclassified samples are labeled. Numbers in parenthesis are sample sizes. The MDS plots use 188 genes when the number of pairwise DEGs is 50. LogFC stands for log-fold-change. The first two leading logFCs were used at the two axes.
Figure 4B:
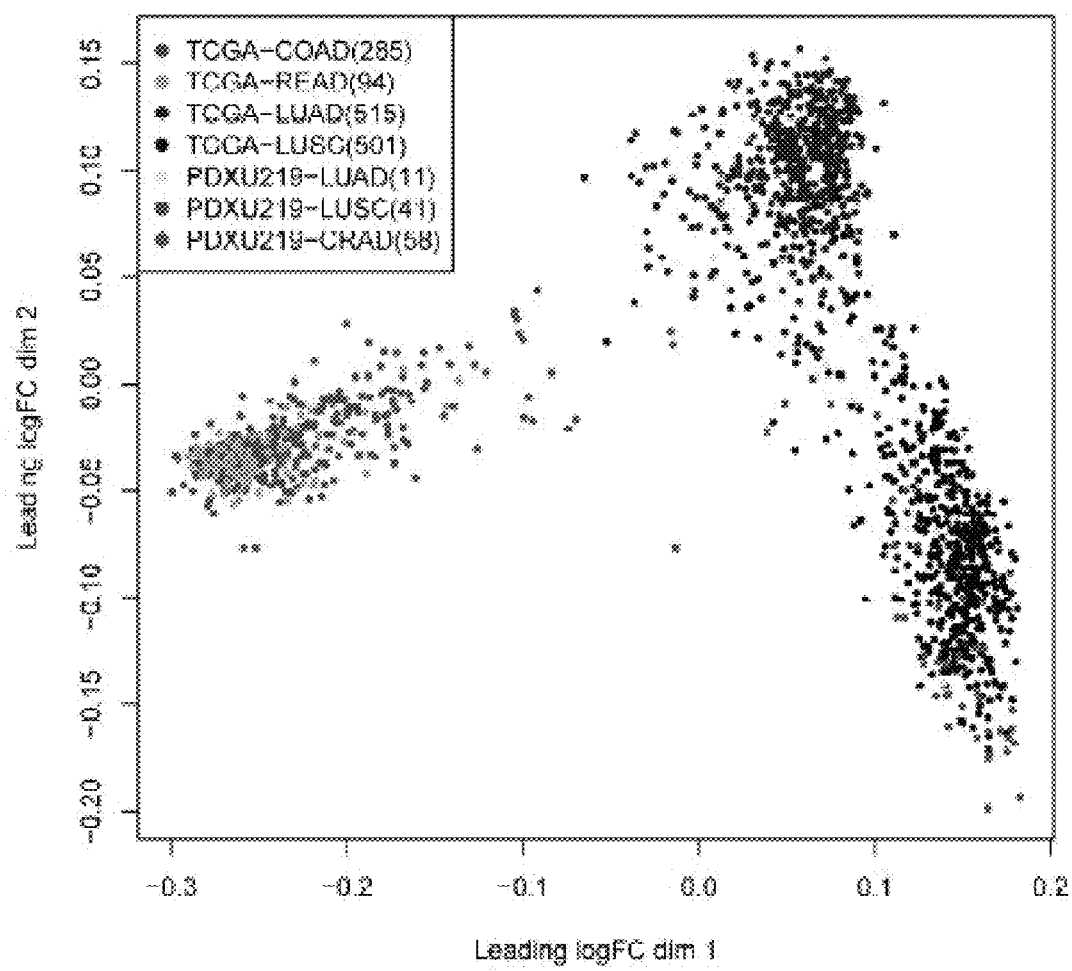
FIG. 4B illustrates multidimensional scaling (MDS) plots of colorectal cancer and lung cancer samples in TCGA and PDXU219. In the PDX dataset, 4 misclassified samples are labeled. Numbers in parenthesis are sample sizes. The MDS plots use 188 genes when the number of pairwise DEGs is 50. LogFC stands for log-fold-change. The first two leading logFCs were used at the two axes.
Figure 4C:
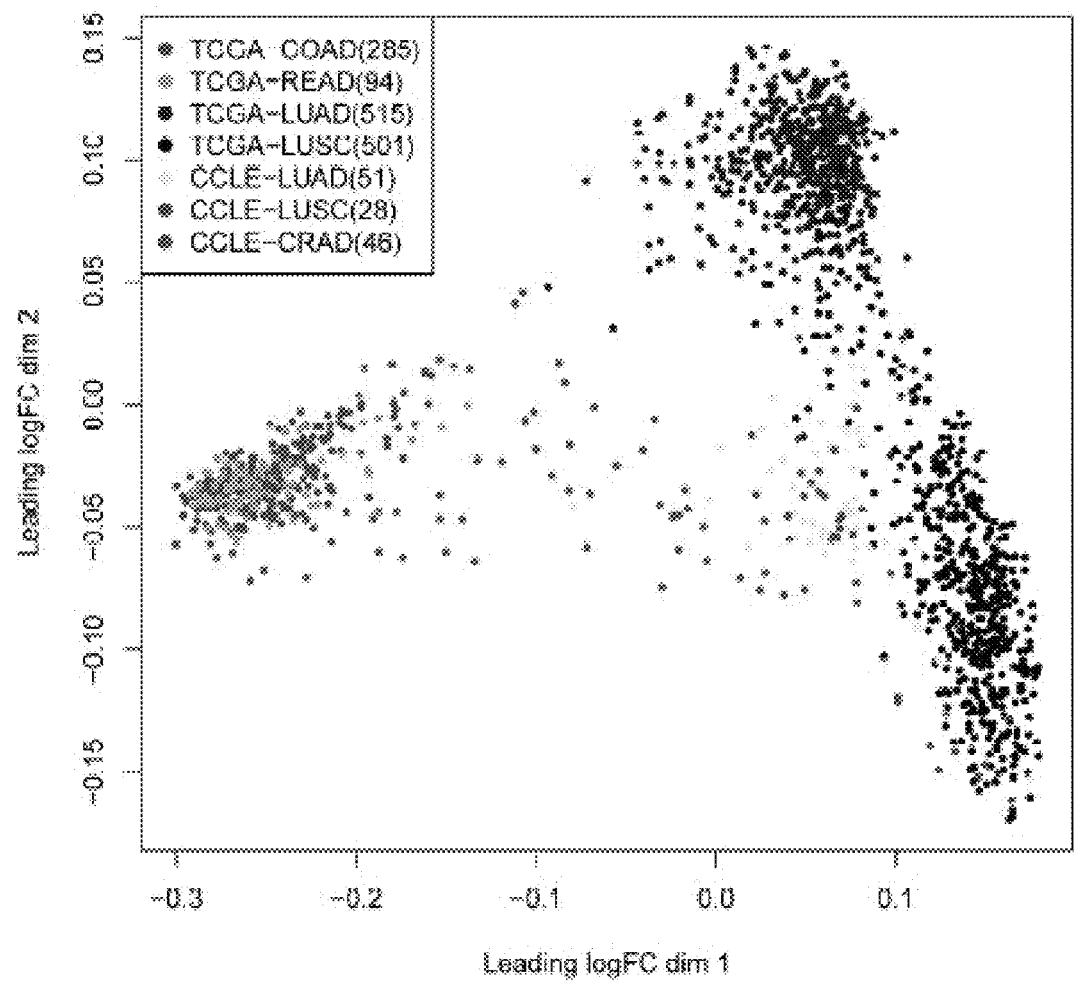
FIG. 4C illustrates multidimensional scaling (MDS) plots of colorectal cancer and lung cancer samples in TCGA and CCLE. In the PDX dataset, 4 misclassified samples are labeled. Numbers in parenthesis are sample sizes. The MDS plots use 188 genes when the number of pairwise DEGs is 50. LogFC stands for log-fold-change. The first two leading logFCs were used at the two axes.

By using the DEGs derived from the pairwise comparisons between TCGA cancer types, we can classify and diagnose malignant diseases of unknown cancer type for both human tumors and PDXs, but unlikely for cell lines. Results from this molecular pathology approach are in good agreement with traditional histopathology, thus forming the basis of a new molecular diagnosis. As an example, we used 188 signature genes from the pairwise comparisons of 4 TCGA cancers (LUAD, LUSC, COAD, and READ) by setting pairwise DEGs to 50. By design and as expected, these signature genes distinguish colorectal cancers from lung cancers in TCGA (FIG. 4A). When applied to both PDX and PDXU219 datasets, we observed that the colorectal PDXs and lung PDXs are clustered with corresponding TCGA cancer samples (FIGS. 4A and 4B). However, in the CCLE dataset, the 3 cancers (CRAD, LUAD, and LUSC) do not show good separation, and they seem to form a widespread cluster by themselves between the TCGA lung cancer and colorectal cancer samples (FIG. 4C). Because both PDXU219 and CCLE were profiled by Affymetrix microarrays, it is unlikely that the dislocation of CCLE samples is a technical artifact, but rather reflective of their transcriptome expression drift from both human and PDX tumors.

Figure 4D:
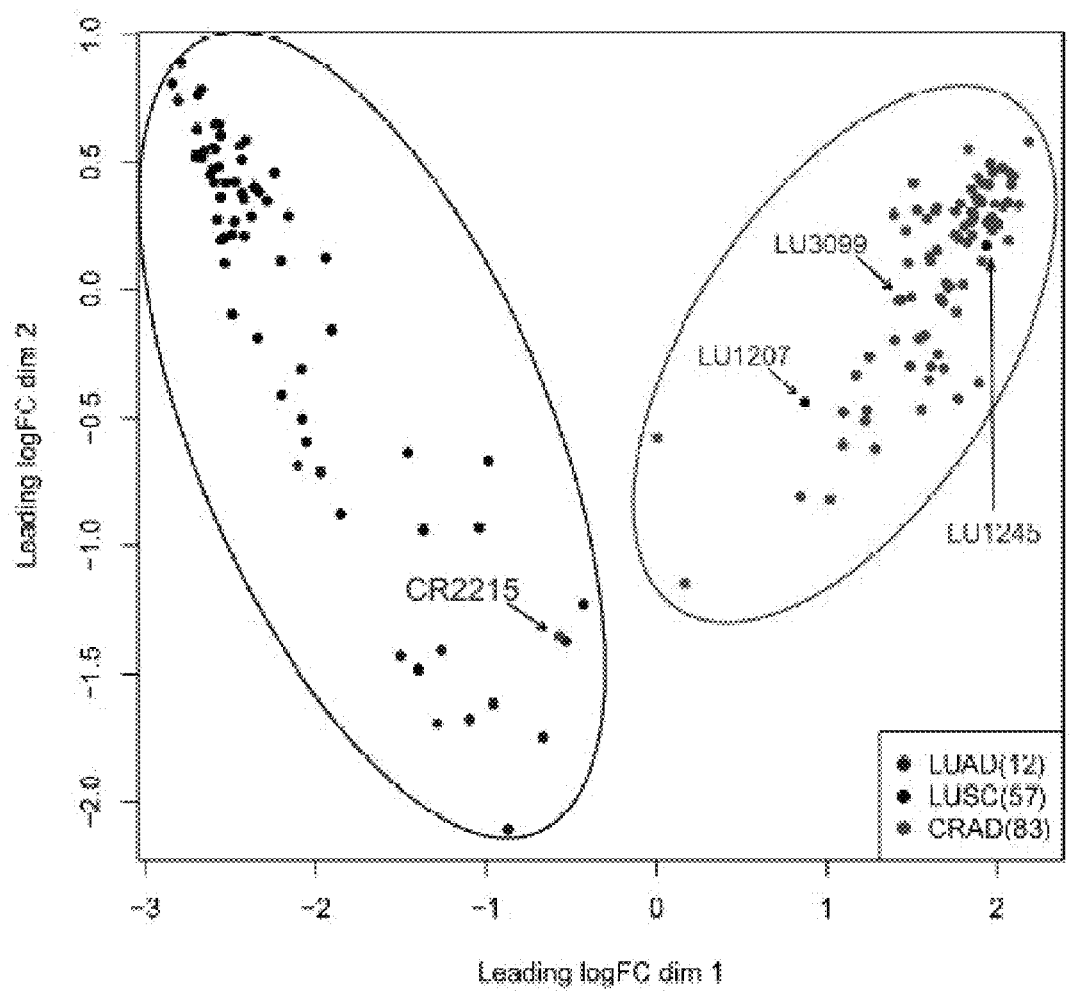
FIG. 4D illustrates multidimensional scaling (MDS) plots of colorectal cancer and lung cancer samples in PDX. In the PDX dataset, 4 misclassified samples are labeled. Numbers in parenthesis are sample sizes. The MDS plots use 188 genes when the number of pairwise DEGs is 50. LogFC stands for log-fold-change. The first two leading logFCs were used at the two axes.

To demonstrate the classification power of our method, we applied the signature DEGs to the PDX dataset and plot the samples by datasets. Again, we observed a clear separation of cancer types (FIG. 4D). We also saw 4 outliers, a colorectal PDX model (CR2215) in the lung cancer group and 3 lung cancer PDX models (LU1207, LU1245, LU3099) in the colorectal cancer group. We performed immunochemistry (IHC) analysis using tissue specific biomarkers (Table 2-3) to confirm their identity. The IHC results demonstrated that the 3 misclassified lung cancer models are indeed colorectal adenocarcinoma (CRAD). The only misclassified CRAD is in fact pancreatic adenocarcinoma (PAAD). Our current interpretation is that the original hospital diagnosis was wrong. Although LU1245, LU3099, and LU1207 were derived from tumors taken from lung and with adenocarcinoma morphology, they were actually the metastasis from primary CRAD. Prior histopathology was not able to identify them correctly since they are all adenocarcinoma with similar morphology.

Our DEG-based method can be used to build machine learning classifiers to diagnose tumors. To illustrate this, we randomly partitioned the 2463 TCGA patient samples into a train dataset and a validation dataset with an 80:20 split ratio. A support vector machine (SVM) based on the 686

DEGs was trained in the train dataset with 5-fold cross-validations, and then tested in the validation dataset. The partition and subsequent processes were repeated 10 times. In both cross validations and test dataset evaluation, the SVM consistently achieved ~98% accuracy if COAD and ROAD samples were treated as the same disease.

TABLE 1

Cell lines used in the analysis

| Cell Line | Cancer_Type | Subtype2 | Classification |
|---|---|---|---|
| CALU3_LUNG | lung | adenocarcinoma | LUAD |
| CORL105_LUNG | lung | adenocarcinoma | LUAD |
| DFCI024_LUNG | lung | adenocarcinoma | LUAD |
| DV90_LUNG | lung | adenocarcinoma | LUAD |
| HCC1833_LUNG | lung | adenocarcinoma | LUAD |
| HCC2108_LUNG | lung | adenocarcinoma | LUAD |
| HCC2279_LUNG | lung | adenocarcinoma | LUAD |
| HCC364_LUNG | lung | adenocarcinoma | LUAD |
| HCC4006_LUNG | lung | adenocarcinoma | LUAD |
| HCC44_LUNG | lung | adenocarcinoma | LUAD |
| HCC78_LUNG | lung | adenocarcinoma | LUAD |
| HCC827GR5_LUNG | lung | adenocarcinoma | LUAD |
| HCC827_LUNG | lung | adenocarcinoma | LUAD |
| HLC1_LUNG | lung | adenocarcinoma | LUAD |
| HS229T_LUNG | lung | adenocarcinoma | LUAD |
| HS618T_LUNG | lung | adenocarcinoma | LUAD |
| LXF289_LUNG | lung | adenocarcinoma | LUAD |
| MORCPR_LUNG | lung | adenocarcinoma | LUAD |
| NCIH1355_LUNG | lung | adenocarcinoma | LUAD |
| NCIH1373_LUNG | lung | adenocarcinoma | LUAD |
| NCIH1395_LUNG | lung | adenocarcinoma | LUAD |
| NCIH1437_LUNG | lung | adenocarcinoma | LUAD |
| NCIH1563_LUNG | lung | adenocarcinoma | LUAD |
| NCIH1573_LUNG | lung | adenocarcinoma | LUAD |
| NCIH1623_LUNG | lung | adenocarcinoma | LUAD |
| NCIH1648_LUNG | lung | adenocarcinoma | LUAD |
| NCIH1651_LUNG | lung | adenocarcinoma | LUAD |
| NCIH1693_LUNG | lung | adenocarcinoma | LUAD |
| NCIH1703_LUNG | lung | adenocarcinoma | LUAD |
| NCIH1734_LUNG | lung | adenocarcinoma | LUAD |
| NCIH1755_LUNG | lung | adenocarcinoma | LUAD |
| NCIH1792_LUNG | lung | adenocarcinoma | LUAD |
| NCIH2009_LUNG | lung | adenocarcinoma | LUAD |
| NCIH2023_LUNG | lung | adenocarcinoma | LUAD |
| NCIH2073_LUNG | lung | adenocarcinoma | LUAD |
| NCIH2085_LUNG | lung | adenocarcinoma | LUAD |
| NCIH2087_LUNG | lung | adenocarcinoma | LUAD |
| NCIH2122_LUNG | lung | adenocarcinoma | LUAD |
| NCIH2126_LUNG | lung | adenocarcinoma | LUAD |
| NCIH2228_LUNG | lung | adenocarcinoma | LUAD |
| NCIH2291_LUNG | lung | adenocarcinoma | LUAD |
| NCIH2342_LUNG | lung | adenocarcinoma | LUAD |
| NCIH2347_LUNG | lung | adenocarcinoma | LUAD |
| NCIH2405_LUNG | lung | adenocarcinoma | LUAD |
| NCIH322_LUNG | lung | adenocarcinoma | LUAD |
| NCIH3255_LUNG | lung | adenocarcinoma | LUAD |
| NCIH441_LUNG | lung | adenocarcinoma | LUAD |
| NCIH854_LUNG | lung | adenocarcinoma | LUAD |
| RERFLCAD1_LUNG | lung | adenocarcinoma | LUAD |
| RERFLCAD2_LUNG | lung | adenocarcinoma | LUAD |
| SKLU1_LUNG | lung | adenocarcinoma | LUAD |
| VMRCLCD_LUNG | lung | adenocarcinoma | LUAD |
| CALU1_LUNG | lung | squamous_cell_carcinoma | LUSC |
| EBC1_LUNG | lung | squamous_cell_carcinoma | LUSC |
| EPLC272H_LUNG | lung | squamous_cell_carcinoma | LUSC |
| HARA_LUNG | lung | squamous_cell_carcinoma | LUSC |
| HCC1588_LUNG | lung | squamous_cell_carcinoma | LUSC |
| HCC15_LUNG | lung | squamous_cell_carcinoma | LUSC |
| HCC1897_LUNG | lung | squamous_cell_carcinoma | LUSC |
| HCC2814_LUNG | lung | squamous_cell_carcinoma | LUSC |
| HCC95_LUNG | lung | squamous_cell_carcinoma | LUSC |
| HLFA_LUNG | lung | squamous_cell_carcinoma | LUSC |
| KNS62_LUNG | lung | squamous_cell_carcinoma | LUSC |
| LC1F_LUNG | lung | squamous_cell_carcinoma | LUSC |
| LC1SQSF_LUNG | lung | squamous_cell_carcinoma | LUSC |
| LK2_LUNG | lung | squamous_cell_carcinoma | LUSC |
| LOUNH91_LUNG | lung | squamous_cell_carcinoma | LUSC |
| LUDLU1_LUNG | lung | squamous_cell_carcinoma | LUSC |
| NCIH1385_LUNG | lung | squamous_cell_carcinoma | LUSC |
| NCIH1869_LUNG | lung | squamous_cell_carcinoma | LUSC |
| NCIH2170_LUNG | lung | squamous_cell_carcinoma | LUSC |
| NCIH226_LUNG | lung | squamous_cell_carcinoma | LUSC |
| NCIH520_LUNG | lung | squamous_cell_carcinoma | LUSC |
| RERFLCAI_LUNG | lung | squamous_cell_carcinoma | LUSC |
| RERFLCSQ1_LUNG | lung | squamous_cell_carcinoma | LUSC |
| SKMES1_LUNG | lung | squamous_cell_carcinoma | LUSC |
| SQ1_LUNG | lung | squamous_cell_carcinoma | LUSC |
| SW1573_LUNG | lung | squamous_cell_carcinoma | LUSC |
| SW900_LUNG | lung | squamous_cell_carcinoma | LUSC |
| VMRCLCP_LUNG | lung | squamous_cell_carcinoma | LUSC |
| C2BBE1_LARGE_INTESTINE | large_intestine | adenocarcinoma | CRAD |
| CCK81_LARGE_INTESTINE | large_intestine | adenocarcinoma | CRAD |
| CL11_LARGE_INTESTINE | large_intestine | adenocarcinoma | CRAD |
| CL34_LARGE_INTESTINE | large_intestine | adenocarcinoma | CRAD |
| COLO201_LARGE_INTESTINE | large_intestine | adenocarcinoma | CRAD |
| COLO205_LARGE_INTESTINE | large_intestine | adenocarcinoma | CRAD |
| COLO320_LARGE_INTESTINE | large_intestine | adenocarcinoma | CRAD |
| COLO678_LARGE_INTESTINE | large_intestine | adenocarcinoma | CRAD |
| DLD1_LARGE_INTESTINE | large_intestine | adenocarcinoma | CRAD |
| GP2D_LARGE_INTESTINE | large_intestine | adenocarcinoma | CRAD |
| HCC56_LARGE_INTESTINE | large_intestine | adenocarcinoma | CRAD |
| HCT15_LARGE_INTESTINE | large_intestine | adenocarcinoma | CRAD |
| HCT8_LARGE_INTESTINE | large_intestine | adenocarcinoma | CRAD |
| HRT18_LARGE_INTESTINE | large_intestine | adenocarcinoma | CRAD |
| HS255T_LARGE_INTESTINE | large_intestine | adenocarcinoma | CRAD |
| HS698T_LARGE_INTESTINE | large_intestine | adenocarcinoma | CRAD |

TABLE 1-continued

Cell lines used in the analysis

| Cell Line | Cancer_Type | Subtype2 | Classification |
|---|---|---|---|
| HT29_LARGE_INTESTINE | large_intestine | adenocarcinoma | CRAD |
| HT55_LARGE_INTESTINE | large_intestine | adenocarcinoma | CRAD |
| KM12_LARGE_INTESTINE | large_intestine | adenocarcinoma | CRAD |
| LOVO_LARGE_INTESTINE | large_intestine | adenocarcinoma | CRAD |
| LS1034_LARGE_INTESTINE | large_intestine | adenocarcinoma | CRAD |
| LS123_LARGE_INTESTINE | large_intestine | adenocarcinoma | CRAD |
| LS180_LARGE_INTESTINE | large_intestine | adenocarcinoma | CRAD |
| LS411N_LARGE_INTESTINE | large_intestine | adenocarcinoma | CRAD |
| LS513_LARGE_INTESTINE | large_intestine | adenocarcinoma | CRAD |
| MDST8_LARGE_INTESTINE | large_intestine | adenocarcinoma | CRAD |
| NCIH508_LARGE_INTESTINE | large_intestine | adenocarcinoma | CRAD |
| NCIH716_LARGE_INTESTINE | large_intestine | adenocarcinoma | CRAD |
| NCIH747_LARGE_INTESTINE | large_intestine | adenocarcinoma | CRAD |
| OUMS23_LARGE_INTESTINE | large_intestine | adenocarcinoma | CRAD |
| RCM1_LARGE_INTESTINE | large_intestine | adenocarcinoma | CRAD |
| RKO_LARGE_INTESTINE | large_intestine | adenocarcinoma | CRAD |
| SKCO1_LARGE_INTESTINE | large_intestine | adenocarcinoma | CRAD |
| SNUC1_LARGE_INTESTINE | large_intestine | adenocarcinoma | CRAD |
| SNUC2A_LARGE_INTESTINE | large_intestine | adenocarcinoma | CRAD |
| SNUC4_LARGE_INTESTINE | large_intestine | adenocarcinoma | CRAD |
| SNUC5_LARGE_INTESTINE | large_intestine | adenocarcinoma | CRAD |
| SW1116_LARGE_INTESTINE | large_intestine | adenocarcinoma | CRAD |
| SW1417_LARGE_INTESTINE | large_intestine | adenocarcinoma | CRAD |
| SW1463_LARGE_INTESTINE | large_intestine | adenocarcinoma | CRAD |
| SW403_LARGE_INTESTINE | large_intestine | adenocarcinoma | CRAD |
| SW480_LARGE_INTESTINE | large_intestine | adenocarcinoma | CRAD |
| SW48_LARGE_INTESTINE | large_intestine | adenocarcinoma | CRAD |
| SW620_LARGE_INTESTINE | large_intestine | adenocarcinoma | CRAD |
| SW837_LARGE_INTESTINE | large_intestine | adenocarcinoma | CRAD |
| SW948_LARGE_INTESTINE | large_intestine | adenocarcinoma | CRAD |
| T84_LARGE_INTESTINE | large_intestine | adenocarcinoma | CRAD |
| ALEXANDERCELLS_LIVER | liver | hepatocellular_carcinoma | LIHC |
| C3A_LIVER | liver | hepatocellular_carcinoma | LIHC |
| HEP3B217_LIVER | liver | hepatocellular_carcinoma | LIHC |
| HEPG2_LIVER | liver | hepatocellular_carcinoma | LIHC |
| HLE_LIVER | liver | hepatocellular_carcinoma | LIHC |
| HLF_LIVER | liver | hepatocellular_carcinoma | LIHC |
| HUH1_LIVER | liver | hepatocellular_carcinoma | LIHC |
| HUH7_LIVER | liver | hepatocellular_carcinoma | LIHC |
| JHH1_LIVER | liver | hepatocellular_carcinoma | LIHC |
| JHH2_LIVER | liver | hepatocellular_carcinoma | LIHC |
| JHH4_LIVER | liver | hepatocellular_carcinoma | LIHC |
| JHH5_LIVER | liver | hepatocellular_carcinoma | LIHC |
| JHH6_LIVER | liver | hepatocellular_carcinoma | LIHC |
| JHH7_LIVER | liver | hepatocellular_carcinoma | LIHC |
| L17_LIVER | liver | hepatocellular_carcinoma | LIHC |
| PLCPRF5_LIVER | liver | hepatocellular_carcinoma | LIHC |
| SNU182_LIVER | liver | hepatocellular_carcinoma | LIHC |
| SNU387_LIVER | liver | hepatocellular_carcinoma | LIHC |
| SNU398_LIVER | liver | hepatocellular_carcinoma | LIHC |
| SNU423_LIVER | liver | hepatocellular_carcinoma | LIHC |
| SNU449_LIVER | liver | hepatocellular_carcinoma | LIHC |
| SNU475_LIVER | liver | hepatocellular_carcinoma | LIHC |
| SNU761_LIVER | liver | hepatocellular_carcinoma | LIHC |
| SNU878_LIVER | liver | hepatocellular_carcinoma | LIHC |
| SNU886_LIVER | liver | hepatocellular_carcinoma | LIHC |
| ASPC1_PANCREAS | pancreas | ductal_carcinoma | PAAD |
| BXPC3_PANCREAS | pancreas | ductal carcinoma | PAAD |
| CAPAN1_PANCREAS | pancreas | ductal carcinoma | PAAD |
| CAPAN2_PANCREAS | pancreas | ductal carcinoma | PAAD |
| CFPAC1_PANCREAS | pancreas | ductal carcinoma | PAAD |
| HPAC_PANCREAS | pancreas | ductal carcinoma | PAAD |
| HPAFII_PANCREAS | pancreas | ductal carcinoma | PAAD |
| HS766T_PANCREAS | pancreas | ductal carcinoma | PAAD |
| KCIMOH1_PANCREAS | pancreas | ductal carcinoma | PAAD |
| KLM1_PANCREAS | pancreas | ductal carcinoma | PAAD |
| KP1NL_PANCREAS | pancreas | ductal carcinoma | PAAD |
| KP1N_PANCREAS | pancreas | ductal carcinoma | PAAD |
| KP3_PANCREAS | pancreas | ductal carcinoma | PAAD |
| KP4_PANCREAS | pancreas | ductal carcinoma | PAAD |
| MIAPACA2_PANCREAS | pancreas | ductal carcinoma | PAAD |
| PANC0327_PANCREAS | pancreas | ductal carcinoma | PAAD |
| PANC0813_PANCREAS | pancreas | ductal carcinoma | PAAD |
| PANC1005_PANCREAS | pancreas | ductal carcinoma | PAAD |
| PANC1_PANCREAS | pancreas | ductal carcinoma | PAAD |

TABLE 1-continued

Cell lines used in the analysis

| Cell Line | Cancer_Type | Subtype2 | Classification |
|---|---|---|---|
| PATU8902_PANCREAS | pancreas | ductal carcinoma | PAAD |
| PATU8988S_PANCREAS | pancreas | ductal carcinoma | PAAD |
| PATU8988T_PANCREAS | pancreas | ductal carcinoma | PAAD |
| PL45_PANCREAS | pancreas | ductal carcinoma | PAAD |
| PSN1_PANCREAS | pancreas | ductal carcinoma | PAAD |
| SU8686_PANCREAS | pancreas | ductal carcinoma | PAAD |
| SUIT2_PANCREAS | pancreas | ductal carcinoma | PAAD |
| SW1990_PANCREAS | pancreas | ductal carcinoma | PAAD |
| T3M4_PANCREAS | pancreas | ductal carcinoma | PAAD |
| BHY_UPPER_AERODIGESTIVE_TRACT | upper_aerodigestive_tract | squamous_cell_carcinoma | HNSC |
| BICR16_UPPER_AERODIGESTIVE_TRACT | upper_aerodigestive_tract | squamous_cell_carcinoma | HNSC |
| BICR18_UPPER_AERODIGESTIVE_TRACT | upper_aerodigestive_tract | squamous_cell_carcinoma | HNSC |
| BICR22_UPPER_AERODIGESTIVE_TRACT | upper_aerodigestive_tract | squamous_cell_carcinoma | HNSC |
| BICR31_UPPER_AERODIGESTIVE_TRACT | upper_aerodigestive_tract | squamous_cell_carcinoma | HNSC |
| BICR56_UPPER_AERODIGESTIVE_TRACT | upper_aerodigestive_tract | squamous_cell_carcinoma | HNSC |
| BICR6_UPPER_AERODIGESTIVE_TRACT | upper_aerodigestive_tract | squamous_cell_carcinoma | HNSC |
| CAL27_UPPER_AERODIGESTIVE_TRACT | upper_aerodigestive_tract | squamous_cell_carcinoma | HNSC |
| CAL33_UPPER_AERODIGESTIVE_TRACT | upper_aerodigestive_tract | squamous_cell_carcinoma | HNSC |
| FADU_UPPER_AERODIGESTIVE_TRACT | upper_aerodigestive_tract | squamous_cell_carcinoma | HNSC |
| HN_UPPER_AERODIGESTIVE_TRACT | upper_aerodigestive_tract | squamous_cell_carcinoma | HNSC |
| HSC2_UPPER_AERODIGESTIVE_TRACT | upper_aerodigestive_tract | squamous_cell_carcinoma | HNSC |
| HSC3_UPPER_AERODIGESTIVE_TRACT | upper_aerodigestive_tract | squamous_cell_carcinoma | HNSC |
| HSC4_UPPER_AERODIGESTIVE_TRACT | upper_aerodigestive_tract | squamous_cell_carcinoma | HNSC |
| PECAPJ15_UPPER_AERODIGESTIVE_TRACT | upper_aerodigestive_tract | squamous_cell_carcinoma | HNSC |
| PECAPJ34CLONEC12_UPPER_AERODIGESTIVE_TRACT | upper_aerodigestive_tract | squamous_cell_carcinoma | HNSC |
| PECAPJ41CLONED2_UPPER_AERODIGESTIVE_TRACT | upper_aerodigestive_tract | squamous_cell_carcinoma | HNSC |
| PECAPJ49_UPPER_AERODIGESTIVE_TRACT | upper_aerodigestive_tract | squamous_cell_carcinoma | HNSC |
| SCC15_UPPER_AERODIGESTIVE_TRACT | upper_aerodigestive_tract | squamous_cell_carcinoma | HNSC |
| SCC25_UPPER_AERODIGESTIVE_TRACT | upper_aerodigestive_tract | squamous_cell_carcinoma | HNSC |
| SCC4_UPPER_AERODIGESTIVE_TRACT | upper_aerodigestive_tract | squamous_cell_carcinoma | HNSC |
| SCC9_UPPER_AERODIGESTIVE_TRACT | upper_aerodigestive_tract | squamous_cell_carcinoma | HNSC |
| SNU1066_UPPER_AERODIGESTIVE_TRACT | upper_aerodigestive_tract | squamous_cell_carcinoma | HNSC |
| SNU1076_UPPER_AERODIGESTIVE_TRACT | upper_aerodigestive_tract | squamous_cell_carcinoma | HNSC |
| SNU1214_UPPER_AERODIGESTIVE_TRACT | upper_aerodigestive_tract | squamous_cell_carcinoma | HNSC |
| SNU46_UPPER_AERODIGESTIVE_TRACT | upper_aerodigestive_tract | squamous_cell_carcinoma | HNSC |
| SNU899_UPPER_AERODIGESTIVE_TRACT | upper_aerodigestive_tract | squamous_cell_carcinoma | HNSC |
| YD10B_UPPER_AERODIGESTIVE_TRACT | upper_aerodigestive_tract | squamous_cell_carcinoma | HNSC |
| YD38_UPPER_AERODIGESTIVE_TRACT | upper_aerodigestive_tract | squamous_cell_carcinoma | HNSC |
| YD8_UPPER_AERODIGESTIVE_TRACT | upper_aerodigestive_tract | squamous_cell_carcinoma | HNSC |

TABLE 2

IHC biomarkers for lung origin and colon origins.

| | Diseases | |
|---|---|---|
| Maker | Colorectal adenocarcinoma | Lung adenocarcinoma |
| CK7 | Rare | + |
| CK20 | + | R |
| CDX2 | + | − |
| TTF1 | − | + |

TABLE 3

IHC analysis of the outlier models

| Original ID | Certified type | Corrected ID | Confirmed markers by IHC |
|---|---|---|---|
| LU1245 | CR | CR1245 | TTF1(−), CDX2(3+), CK7(−), CK20(3+) |
| LU3099 | CR | CR3099 | CK(−), TTF1(−), CK20(3+) |

REFERENCES

1. Hoadley K A, Yau C, Wolf D M, Cherniack A D, Tamborero D, Ng S, et al. Multiplatform analysis of 12 cancer types reveals molecular classification within and across tissues of origin. Cell 2014; 158(4):929-44.
2. Comprehensive molecular characterization of gastric adenocarcinoma. Nature 2014; 513(7517):202-9.

3. Comprehensive genomic characterization defines human glioblastoma genes and core pathways. Nature 2008; 455(7216):1061-8.
4. Ge L, Shao G R, Wang H J, Song S L, Xin G, Wu M, et al. Integrated analysis of gene expression profile and genetic variations associated with ovarian cancer. Eur Rev Med Pharmacol Sci 2015; 19(14):2703-10.
5. Tentler J J, Tan A C, Weekes C D, Jimeno A, Leong S, Pitts T M, et al. Patient-derived tumour xenografts as models for oncology drug development. Nat Rev Clin Oncol 2012; 9(6):338-50.
6. Ding L, Ellis M J, Li S, Larson D E, Chen K, Wallis J W, et al. Genome remodelling in a basal-like breast cancer metastasis and xenograft. Nature 2010; 464(7291):999-1005.
7 Yang M, Shan B, Li Q, Song X, Cai J, Deng J, et al. Overcoming erlotinib resistance with tailored treatment regimen in patient-derived xenografts from naive Asian NSCLC patients. International journal of cancer Journal international du cancer 2013; 132 (2):E74-84.
8. Zhang L, Yang J, Cai J, Song X, Deng J, Huang X, et al. A subset of gastric cancers with EGFR amplification and overexpression respond to cetuximab therapy. Sci Rep 2013; 3:2992.
9. Walter A O, Sjin R T, Haringsma H J, Ohashi K, Sun J, Lee K, et al. Discovery of a mutant-selective covalent inhibitor of EGFR that overcomes T790M-mediated resistance in NSCLC. Cancer discovery 2013; 3(12): 1404-15.
10. Jiang J, Wang D D, Yang M, Chen D, Pang L, Guo S, et al. Comprehensive characterization of chemotherapeutic efficacy on metastases in the established gastric neuroendocrine cancer patient derived xenograft model. Oncotarget 2015; 6(17):15639-51.
11. Bladt F, Friese-Hamim M, Ihling C, Wilm C, Blaukat A. The c-Met Inhibitor MSC2156119J Effectively Inhibits Tumor Growth in Liver Cancer Models. Cancers (Basel) 2014; 6(3):1736-52.
12. Chen D, Huang X, Cai J, Guo S, Qian W, Wery J P, et al. A set of defined oncogenic mutation alleles seems to better predict the response to cetuximab in CRC patient-derived xenograft than KRAS 12/13 mutations. Oncotarget 2015; 6(38):40815-21.
13. Robinson M D, Smyth G K. Small-sample estimation of negative binomial dispersion, with applications to SAGE data. Biostatistics 2008; 9(2):321-32.
14. Barretina J, Caponigro G, Stransky N, Venkatesan K, Margolin A A, Kim S, et al. The Cancer Cell Line Encyclopedia enables predictive modelling of anticancer drug sensitivity. Nature 2012; 483(7391):603-7.
15. Akashi Y, Oda T, Ohara Y, Miyamoto R, Hashimoto S, Enomoto T, et al. Histological advantages of the tumor graft: a murine model involving transplantation of human pancreatic cancer tissue fragments. Pancreas 2013; 42(8): 1275-82.
16. Daniel V C, Marchionni L, Hierman J S, Rhodes J T, Devereux W L, Rudin C M, et al. A primary xenograft model of small-cell lung cancer reveals irreversible changes in gene expression imposed by culture in vitro. Cancer research 2009; 69(8):3364-73.
17. Johnson J I, Decker S, Zaharevitz D, Rubinstein L V, Venditti J M, Schepartz S, et al. Relationships between drug activity in NCI preclinical in vitro and in vivo models and early clinical trials. British journal of cancer 2001; 84(10):1424-31.
18. Voskoglou-Nomikos T, Pater J L, Seymour L. Clinical predictive value of the in vitro cell line, human xenograft, and mouse allograft preclinical cancer models. Clinical cancer research: an official journal of the American Association for Cancer Research 2003; 9(11):4227-39.
19. Drost J, van Jaarsveld R H, Ponsioen B, Zimberlin C, van Boxtel R, Buijs A, et al. Sequential cancer mutations in cultured human intestinal stem cells. Nature 2015; 521(7550):43-7.
20. Chua C W, Shibata M, Lei M, Toivanen R, Barlow L J, Bergren S K, et al. Single luminal epithelial progenitors can generate prostate organoids in culture. Nature cell biology 2014; 16(10):951-61, 1-4.

What is claimed is:

1. A method for treating cancer in a subject comprising:
obtaining a first gene expression profile of a first cancer sample having a first cancer type, wherein the first cancer type is selected from the group consisting of colon cancer, rectal cancer, head and neck cancer, and lung cancer;
obtaining a second gene expression profile of a second cancer sample having a second cancer type, wherein the second cancer type is different from the first cancer type;
obtaining a third gene expression profile of a third cancer sample having a third cancer type, wherein the third cancer type is different from the first and the second cancer type;
comparing said first gene expression profile with said second gene expression profile;
selecting $N_1$ genes that are most differentially expressed in the first and the second gene expression profiles to generate first pairwise differentially expressed genes (DEGs), wherein $N_1$ is an integer between 10 and 100;
comparing said first gene expression profile with said third gene expression profile;
selecting $N_2$ genes that are most differentially expressed in the first and the third gene expression profiles to generate second pairwise DEGs, wherein $N_2$ is an integer between 10 and 100;
comparing said second gene expression profile with said third gene expression profile;
selecting $N_3$ genes that are most differentially expressed in the second and the third gene expression profiles to generate third pairwise DEGs, wherein $N_3$ is an integer between 10 and 100;
generating a set of signature genes that comprises the first, second and third pairwise DEGs;
generating a machine learning classifier based on the set of signature genes, wherein the machine learning classifier receives an input comprising expression levels of the set of signature genes and provides an output comprising cancer type;
obtaining a sample from the subject;
obtaining expression levels of the set of signature genes in the sample;
determining that the subject has a cancer of the first cancer type based on the expression levels of the set of signature genes in the subject sample using the machine learning classifier; and
administering to the subject a therapeutically effective amount of a drug suitable for treating the first cancer type,
wherein the drug is selected from the group consisting of (a) Bevacizumab, Capecitabine, Cetuximab, 5-FU, Fluorouracil Injection, Irinotecan hydrochloride, Leucovorin Calcium, Oxaliplatin, Panitumumab, Ramucirumab, Regorafenib, Trifluridine and Tipiracil hydrochloride, and Ziv-aflibercept when the first cancer type is colon cancer or rectal cancer, (b) Bleomycin, Cetuximab, Docetaxel, Hydroxyurea, Methotrexate, and Pembrolizumab when the first cancer type is head and neck cancer, and (c) Afatinib dimaleate, Alectinib, Bevacizumab, Carboplatin, Ceritinib, Docetaxel, Erlotinib, Everolimus, Gefitinib, Gemcitabine Hydrochloride, Mechlorethamine hydrochloride, Methotrexate, Necitumumab, Nivolumab, Osimertinib, Paclitaxel, Pembrolizumab, Pemetrexed disodium, Ramucirumab, and Vinorelbine Tartrate when the first cancer type is lung cancer.

2. The method of claim 1, wherein the first, second or third cancer sample is a surgical removal sample or biopsy sample from a cancer patient or a patient derived xenograft (PDX).

3. The method of claim 1, wherein $N_1=N_2=N_3$.

4. The method of claim 1, wherein $N_1$, $N_2$ or $N_3$ are around 50.

5. The method of claim 1, wherein the first gene expression profile, the second gene profile or the third gene profile is obtained by transcriptome RNA sequencing or microarray.

6. The method of claim 1, wherein the first gene expression profile, the second gene profile or the third gene profile is obtained from the cancer genome atlas (TCGA) dataset.

7. The method of claim 1, wherein the $N_1$, $N_2$ or $N_3$ genes most differentially expressed are selected by ranking using t-test, or Mann-Whitney U test.

8. The method of claim 1, wherein the second or third cancer type is acute lymphoblastic leukemia (ALL), acute myeloid leukemia, adrenocortical carcinoma, anal cancer, astrocytoma, childhood cerebellar or cerebral, basal-cell carcinoma, bile duct cancer, bladder cancer, bone tumor, brain cancer, cerebellar astrocytoma, cerebral astrocytoma/malignant glioma, ependymoma, medulloblastoma, supratentorial primitive neuroectodermal tumors, visual pathway and hypothalamic glioma, breast cancer, Burkitt's lymphoma, cervical cancer, chronic lymphocytic leukemia, chronic myelogenous leukemia, colon cancer, emphysema, endometrial cancer, ependymoma, esophageal cancer, Ewing's sarcoma, retinoblastoma, gastric (stomach) cancer, glioma, head and neck cancer, heart cancer, Hodgkin lymphoma, islet cell carcinoma (endocrine pancreas), Kaposi sarcoma, kidney cancer, laryngeal cancer, leukaemia, liver cancer, lung cancer, neuroblastoma, non-Hodgkin lymphoma, ovarian cancer, pancreatic cancer, pharyngeal cancer, prostate cancer, rectal cancer, renal cell carcinoma (kidney cancer), retinoblastoma, Ewing family of tumors, skin cancer, stomach cancer, testicular cancer, throat cancer, thyroid cancer, vaginal cancer, colon adenocarcinoma, rectum adenocarcinoma, lung adenocarcinoma, lung squamous cell carcinoma, head and neck squamous cell carcinoma, liver hepatocellular carcinoma, or pancreatic adenocarcinoma.

9. The method of claim 1, wherein the set of signature genes has m genes, wherein m is an integer between 5 to 5000.

10. The method of claim 1, wherein the machine learning classifier is a support vector machine.

* * * * *